(12) United States Patent
Boyd et al.

(10) Patent No.: US 8,641,649 B2
(45) Date of Patent: Feb. 4, 2014

(54) PUMP FOR DENTAL WATER JET

(75) Inventors: Brian Boyd, Fort Collins, CO (US);
Brian R. Williams, Fort Collins, CO (US); Kurt M. Taylor, Fort Collins, CO (US)

(73) Assignee: Water Pik, Inc., Fort Collins, CO (US)

( * ) Notice: Subject to any disclaimer, the term of this patent is extended or adjusted under 35 U.S.C. 154(b) by 894 days.

(21) Appl. No.: 12/824,001

(22) Filed: Jun. 25, 2010

(65) Prior Publication Data

US 2010/0261134 A1 Oct. 14, 2010

Related U.S. Application Data

(62) Division of application No. 11/361,749, filed on Feb. 24, 2006, now abandoned.

(51) Int. Cl.
*A61H 13/00* (2006.01)
*A61C 17/02* (2006.01)
*A61H 9/00* (2006.01)

(52) U.S. Cl.
USPC ............................ 601/162; 601/160; 433/95

(58) Field of Classification Search
USPC ............... 601/154–165; 433/80–101; 74/390, 74/392, 395–397, 406, 412 R, 413; 415/124.2
See application file for complete search history.

(56) References Cited

U.S. PATENT DOCUMENTS

| | | | |
|---|---|---|---|
| 555,588 A | 3/1896 | Spencer | |
| 1,278,225 A | 9/1918 | Schamberg | |
| 1,498,267 A | 6/1924 | Hachman | |
| 1,650,686 A | 11/1927 | Binks | |
| 1,681,320 A | 8/1928 | Bergl et al. | |
| 1,933,454 A | 10/1933 | Sidney | |
| 2,107,686 A | 2/1938 | Bramsen et al. | |
| 2,669,233 A | 2/1954 | Friend | |
| 2,794,437 A | 6/1954 | Tash | |
| 2,782,653 A * | 2/1957 | Turner et al. | 74/392 |
| 2,783,919 A | 3/1957 | Ansell | |
| 2,984,452 A | 5/1961 | Hooper | |

(Continued)

FOREIGN PATENT DOCUMENTS

| | | |
|---|---|---|
| CA | 851479 | 9/1970 |
| CH | 655237 | 4/1987 |

(Continued)

OTHER PUBLICATIONS

Waterpik SinuSense, Website: http://www.insightsbyapril.com/2012/03/waterpik-natural-remedy-for-sinus.html, retrieved on May 31, 2012.

(Continued)

*Primary Examiner* — Clinton T Ostrup
*Assistant Examiner* — Christopher Miller
(74) *Attorney, Agent, or Firm* — Dorsey & Whitney LLP

(57) ABSTRACT

A pump for an oral irrigator includes a pump chassis, an eccentric end plate movably connected to the pump chassis, a first alignment shaft connected to the pump chassis, a second alignment shaft connected to the eccentric end plate, a first gear rotating around a longitudinal axis of the first alignment shaft, and a second gear engaging the first gear and rotating around a longitudinal axis of the second alignment shaft. By selectively moving the eccentric end plate relative to the pump chassis selectively moves the second gear relative to the first gear.

18 Claims, 17 Drawing Sheets

(56) References Cited

U.S. PATENT DOCUMENTS

| | | |
|---|---|---|
| 3,089,490 A | 5/1963 | Goldberg |
| 3,096,913 A | 7/1963 | Jousson |
| 3,144,867 A | 8/1964 | Trupp et al. |
| 3,209,956 A | 10/1965 | McKenzie |
| 3,216,619 A | 11/1965 | Richards et al. |
| 3,225,759 A | 12/1965 | Drapen et al. |
| 3,227,158 A | 1/1966 | Mattingly |
| 3,241,386 A * | 3/1966 | Booth .......................... 74/396 |
| 3,297,558 A | 1/1967 | Hillquist |
| D208,778 S | 10/1967 | Koch |
| D209,395 S | 11/1967 | Gilbert |
| 3,370,214 A | 2/1968 | Aymar |
| 3,391,696 A | 7/1968 | Woodward |
| 3,400,999 A | 9/1968 | Goldstein |
| 3,418,552 A | 12/1968 | Holmes |
| 3,420,228 A | 1/1969 | Kalbfeld |
| 3,453,969 A | 7/1969 | Mattingly |
| 3,465,751 A | 9/1969 | Powers |
| 3,487,828 A | 1/1970 | Troy |
| 3,489,268 A | 1/1970 | Meierhoefer |
| 3,496,933 A * | 2/1970 | Lloyd .......................... 601/162 |
| 3,499,440 A | 3/1970 | Gibbs |
| 3,501,203 A | 3/1970 | Falk |
| 3,502,072 A | 3/1970 | Stillman |
| 3,517,669 A | 6/1970 | Buono et al. |
| D218,270 S | 8/1970 | Soper |
| 3,522,801 A | 8/1970 | Robinson |
| 3,536,065 A | 10/1970 | Moret |
| 3,537,444 A | 11/1970 | Garn |
| 3,538,950 A | 11/1970 | Porteners |
| 3,547,110 A | 12/1970 | Balamuth |
| 3,572,375 A | 3/1971 | Rosenberg |
| 3,578,884 A | 5/1971 | Jacobson |
| 3,583,609 A | 6/1971 | Oppenheimer |
| 3,590,813 A | 7/1971 | Roszyk |
| 3,608,548 A | 9/1971 | Lewis |
| 3,636,947 A | 1/1972 | Balamuth |
| 3,651,576 A | 3/1972 | Massa |
| 3,669,101 A | 6/1972 | Kleiner |
| 3,703,170 A | 11/1972 | Ryckman, Jr. |
| 3,747,595 A | 7/1973 | Grossan |
| 3,768,472 A | 10/1973 | Hodosh et al. |
| 3,783,364 A | 1/1974 | Gallanis et al. |
| 3,809,977 A | 5/1974 | Balamuth et al. |
| 3,820,532 A | 6/1974 | Eberhardt et al. |
| 3,827,147 A | 8/1974 | Condon |
| 3,840,795 A | 10/1974 | Roszyk et al. |
| 3,854,209 A | 12/1974 | Franklin et al. |
| 3,874,506 A | 4/1975 | Hill et al. |
| 3,912,125 A | 10/1975 | Acklin |
| 3,943,628 A | 3/1976 | Kronman et al. |
| 3,973,558 A | 8/1976 | Stouffer et al. |
| 4,001,526 A | 1/1977 | Olson |
| 4,004,302 A | 1/1977 | Hori |
| 4,007,739 A | 2/1977 | Bron et al. |
| D246,667 S | 12/1977 | Mackay et al. |
| 4,060,870 A | 12/1977 | Cannarella |
| 4,075,761 A | 2/1978 | Behne et al. |
| 4,078,558 A | 3/1978 | Woog et al. |
| 4,108,167 A * | 8/1978 | Hickman et al. ............... 601/162 |
| 4,108,178 A | 8/1978 | Betush |
| 4,109,650 A | 8/1978 | Peclard |
| 4,141,352 A | 2/1979 | Ebner et al. |
| 4,144,646 A | 3/1979 | Takemoto et al. |
| 4,149,315 A | 4/1979 | Page, Jr. et al. |
| 4,154,375 A | 5/1979 | Bippus |
| 4,160,383 A | 7/1979 | Rauschenberger |
| 4,182,038 A | 1/1980 | Fleer |
| 4,201,200 A | 5/1980 | Hubner |
| 4,215,476 A | 8/1980 | Armstrong |
| 4,219,618 A | 8/1980 | Leonard |
| 4,227,878 A | 10/1980 | Lohn |
| 4,229,634 A | 10/1980 | Hickman et al. |
| 4,236,889 A | 12/1980 | Wright |
| 4,248,589 A | 2/1981 | Lewis |
| 4,249,899 A | 2/1981 | Davis |
| 4,262,799 A | 4/1981 | Perrett |
| 4,266,934 A | 5/1981 | Pernot |
| 4,276,023 A | 6/1981 | Phillips et al. |
| 4,276,880 A | 7/1981 | Malmin |
| 4,302,186 A | 11/1981 | Cammack et al. |
| 4,303,064 A | 12/1981 | Buffa |
| 4,303,070 A | 12/1981 | Ichikawa et al. |
| 4,315,741 A | 2/1982 | Reichl |
| 4,319,568 A | 3/1982 | Tregoning |
| 4,331,422 A | 5/1982 | Heyman |
| 4,337,040 A | 6/1982 | Cammack et al. |
| 4,340,365 A | 7/1982 | Pisanu |
| 4,340,368 A | 7/1982 | Lococo |
| D266,117 S | 9/1982 | Oberheim |
| 4,363,626 A | 12/1982 | Schmidt et al. |
| 4,365,376 A | 12/1982 | Oda et al. |
| 4,370,131 A | 1/1983 | Banko |
| 4,374,354 A | 2/1983 | Petrovic et al. |
| 4,382,167 A | 5/1983 | Maruyama et al. |
| 4,382,786 A | 5/1983 | Lohn |
| D270,000 S | 8/1983 | Ketler |
| 4,412,823 A | 11/1983 | Sakai et al. |
| 4,442,830 A | 4/1984 | Markau |
| 4,442,831 A | 4/1984 | Trenary |
| 4,452,238 A | 6/1984 | Kerr |
| 4,454,866 A | 6/1984 | Fayen |
| 4,512,769 A | 4/1985 | Kozam et al. |
| 4,517,962 A | 5/1985 | Heckele |
| 4,531,912 A | 7/1985 | Schuss et al. |
| 4,531,913 A | 7/1985 | Taguchi |
| 4,532,822 A * | 8/1985 | Godlewski ...................... 74/397 |
| 4,534,340 A | 8/1985 | Kerr et al. |
| 4,552,130 A | 11/1985 | Kinoshita |
| D283,374 S | 4/1986 | Cheuk-Yiu |
| 4,585,415 A | 4/1986 | Hommann |
| 4,591,777 A | 5/1986 | McCarty et al. |
| 4,592,728 A | 6/1986 | Davis |
| 4,602,906 A | 7/1986 | Grunenfelder |
| 4,607,627 A | 8/1986 | Leber et al. |
| 4,613,074 A | 9/1986 | Schulze |
| 4,619,612 A | 10/1986 | Weber et al. |
| 4,629,425 A | 12/1986 | Detsch |
| 4,636,198 A | 1/1987 | Stade |
| 4,644,937 A | 2/1987 | Hommann |
| 4,645,488 A | 2/1987 | Matukas |
| 4,647,831 A | 3/1987 | O'Malley et al. |
| 4,648,838 A | 3/1987 | Schlachter |
| 4,650,475 A | 3/1987 | Smith et al. |
| 4,655,198 A | 4/1987 | Hommann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,770,632 A | 9/1988 | Ryder et al. |
| 4,783,321 A | 11/1988 | Spence |
| 4,787,845 A | 11/1988 | Valentine |
| 4,787,847 A | 11/1988 | Martin et al. |
| 4,793,200 A * | 12/1988 | McDonald ...................... 74/331 |
| 4,798,292 A | 1/1989 | Hauze |
| 4,803,974 A | 2/1989 | Powell |
| 4,804,364 A | 2/1989 | Dieras et al. |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A | 5/1989 | Fujimura et al. |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Lih-Sheng |
| 4,869,720 A | 9/1989 | Chernack |
| 4,880,382 A | 11/1989 | Moret et al. |
| 4,886,452 A | 12/1989 | Lohn |
| 4,900,252 A | 2/1990 | Liefke et al. |
| 4,902,225 A | 2/1990 | Lohn |
| 4,903,687 A | 2/1990 | Lih-Sheng |
| 4,906,187 A | 3/1990 | Amadera |

(56) References Cited

U.S. PATENT DOCUMENTS

| | | |
|---|---|---|
| 4,907,744 A | 3/1990 | Jousson |
| 4,925,450 A | 5/1990 | Imonti et al. |
| 4,928,675 A | 5/1990 | Thornton |
| 4,930,660 A | 6/1990 | Porteous |
| 4,941,459 A | 7/1990 | Mathur |
| 4,950,159 A | 8/1990 | Hansen |
| 4,958,629 A * | 9/1990 | Peace et al. ............. 601/165 |
| 4,958,751 A | 9/1990 | Curtis et al. |
| 4,961,698 A | 10/1990 | Vlock |
| 4,966,551 A | 10/1990 | Betush |
| 4,969,874 A | 11/1990 | Michel et al. |
| 4,973,247 A | 11/1990 | Varnes et al. |
| 4,973,250 A | 11/1990 | Milman |
| 4,975,054 A | 12/1990 | Esrock |
| 4,979,503 A | 12/1990 | Chernack |
| 4,979,504 A | 12/1990 | Mills |
| 4,989,590 A | 2/1991 | Baum et al. |
| 4,998,880 A | 3/1991 | Nerli |
| 5,013,241 A | 5/1991 | Von Gutfeld et al. |
| 5,014,884 A | 5/1991 | Wunsch |
| 5,019,054 A | 5/1991 | Clement et al. |
| 5,027,798 A | 7/1991 | Primiano |
| 5,029,576 A | 7/1991 | Evans, Sr. |
| 5,033,961 A | 7/1991 | Kankler et al. |
| D318,918 S | 8/1991 | Hartwein |
| 5,046,486 A | 9/1991 | Grulke et al. |
| 5,049,071 A | 9/1991 | Davis et al. |
| 5,060,825 A | 10/1991 | Palmer et al. |
| 5,064,168 A | 11/1991 | Raines et al. |
| 5,082,443 A | 1/1992 | Lohn |
| 5,086,756 A | 2/1992 | Powell |
| 5,095,893 A | 3/1992 | Rawden, Jr. |
| 5,098,291 A | 3/1992 | Curtis et al. |
| 5,125,835 A | 6/1992 | Young |
| 5,127,831 A | 7/1992 | Bab |
| 5,142,723 A | 9/1992 | Lustig et al. |
| 5,150,841 A | 9/1992 | Silvenis et al. |
| 5,172,810 A | 12/1992 | Brewer |
| 5,173,273 A | 12/1992 | Brewer |
| 5,183,035 A | 2/1993 | Weir |
| 5,197,458 A | 3/1993 | Ito et al. |
| 5,197,460 A | 3/1993 | Ito et al. |
| 5,199,871 A | 4/1993 | Young |
| 5,203,697 A | 4/1993 | Malmin |
| 5,203,769 A | 4/1993 | Clement et al. |
| 5,204,004 A | 4/1993 | Johnston et al. |
| 5,208,933 A | 5/1993 | Lustig et al. |
| 5,218,956 A | 6/1993 | Handler et al. |
| 5,220,914 A | 6/1993 | Thompson |
| 5,228,646 A | 7/1993 | Raines |
| 5,230,624 A | 7/1993 | Wolf et al. |
| 5,232,687 A | 8/1993 | Geimer |
| 5,235,968 A | 8/1993 | Woog |
| 5,241,714 A | 9/1993 | Barry |
| 5,246,367 A | 9/1993 | Ito et al. |
| 5,252,064 A | 10/1993 | Baum et al. |
| 5,257,933 A | 11/1993 | Jousson |
| D341,943 S | 12/1993 | Si-Hoe |
| 5,267,586 A | 12/1993 | Jankavaara |
| 5,269,684 A | 12/1993 | Fischer |
| 5,281,137 A | 1/1994 | Jousson |
| 5,281,139 A | 1/1994 | Frank et al. |
| 5,282,745 A | 2/1994 | Wiltrout et al. |
| 5,286,192 A | 2/1994 | Dixon |
| 5,286,201 A | 2/1994 | Yu |
| 5,297,962 A | 3/1994 | O'Connor et al. |
| D346,212 S | 4/1994 | Hosl |
| 5,302,123 A | 4/1994 | Bechard |
| 5,317,691 A | 5/1994 | Traeger |
| 5,321,865 A | 6/1994 | Kaeser |
| 5,331,704 A | 7/1994 | Rosen et al. |
| 5,344,317 A | 9/1994 | Pacher et al. |
| 5,346,677 A | 9/1994 | Risk |
| D351,892 S | 10/1994 | Wolf et al. |
| 5,360,338 A | 11/1994 | Waggoner |
| 5,368,548 A | 11/1994 | Jousson |
| 5,370,534 A | 12/1994 | Wolf et al. |
| D354,168 S | 1/1995 | Hartwein |
| 5,378,149 A | 1/1995 | Stropko |
| 5,380,201 A | 1/1995 | Kawata |
| D356,864 S | 3/1995 | Woog |
| 5,399,089 A * | 3/1995 | Eichman et al. ............. 433/80 |
| D358,883 S | 5/1995 | Vos |
| 5,456,672 A | 10/1995 | Diederich et al. |
| 5,465,445 A | 11/1995 | Yeh |
| 5,468,148 A | 11/1995 | Ricks |
| 5,470,305 A * | 11/1995 | Arnett et al. ............. 601/161 |
| 5,474,450 A | 12/1995 | Chronister |
| 5,474,451 A | 12/1995 | Dalrymple et al. |
| 5,476,379 A | 12/1995 | Disel |
| 5,484,281 A | 1/1996 | Renow et al. |
| 5,487,877 A | 1/1996 | Choi |
| 5,490,779 A | 2/1996 | Malmin |
| 5,505,916 A | 4/1996 | Berry, Jr. |
| D369,656 S | 5/1996 | Vos |
| 5,525,058 A | 6/1996 | Gallant et al. |
| 5,526,841 A | 6/1996 | Detsch et al. |
| 5,540,587 A | 7/1996 | Malmin |
| 5,547,374 A | 8/1996 | Coleman |
| D373,631 S | 9/1996 | Maeda et al. |
| 5,554,025 A | 9/1996 | Kinsel |
| 5,556,001 A | 9/1996 | Weissman et al. |
| 5,564,629 A | 10/1996 | Weissman et al. |
| 5,616,028 A | 4/1997 | Hafele et al. |
| 5,634,791 A * | 6/1997 | Matsuura et al. ............. 433/87 |
| 5,636,987 A | 6/1997 | Serfaty |
| 5,640,735 A | 6/1997 | Manning |
| 5,653,591 A | 8/1997 | Loge |
| 5,667,483 A | 9/1997 | Santos |
| 5,683,192 A | 11/1997 | Kilfoil |
| 5,685,197 A * | 11/1997 | Baker et al. ............. 74/409 |
| 5,685,829 A | 11/1997 | Allen |
| 5,685,851 A | 11/1997 | Murphy et al. |
| 5,697,784 A | 12/1997 | Hafele et al. |
| 5,709,545 A | 1/1998 | Johnston et al. |
| 5,716,007 A | 2/1998 | Nottingham et al. |
| 5,718,668 A | 2/1998 | Arnett et al. |
| 5,746,595 A | 5/1998 | Ford |
| 5,749,726 A | 5/1998 | Kinsel |
| 5,759,502 A | 6/1998 | Spencer et al. |
| 5,779,654 A | 7/1998 | Foley et al. |
| 5,795,153 A | 8/1998 | Rechmann |
| 5,819,588 A * | 10/1998 | Deane et al. ............. 74/409 |
| 5,836,030 A | 11/1998 | Hazeu et al. |
| 5,851,079 A | 12/1998 | Horstman et al. |
| D403,511 S | 1/1999 | Serbinski |
| D406,334 S | 3/1999 | Rosenthal et al. |
| 5,876,201 A | 3/1999 | Wilson et al. |
| 5,901,397 A | 5/1999 | Häfele et al. |
| 5,934,902 A | 8/1999 | Abahusayn |
| D413,975 S | 9/1999 | Maeda |
| D417,082 S | 11/1999 | Classen et al. |
| 5,993,402 A | 11/1999 | Sauer et al. |
| 6,030,215 A | 2/2000 | Ellion et al. |
| 6,035,736 A * | 3/2000 | Gyllner et al. ............. 74/397 |
| 6,039,180 A | 3/2000 | Grant |
| D425,615 S | 5/2000 | Bachman et al. |
| D425,981 S | 5/2000 | Bachman et al. |
| 6,056,710 A | 5/2000 | Bachman et al. |
| D426,633 S | 6/2000 | Bachman et al. |
| 6,089,865 A | 7/2000 | Edgar |
| 6,124,699 A | 9/2000 | Suzuki et al. |
| D434,500 S | 11/2000 | Pollock et al. |
| 6,159,006 A | 12/2000 | Cook et al. |
| 6,164,967 A | 12/2000 | Sale et al. |
| D435,905 S | 1/2001 | Bachman et al. |
| 6,193,512 B1 | 2/2001 | Wallace |
| 6,193,932 B1 | 2/2001 | Wu et al. |
| 6,199,239 B1 | 3/2001 | Dickerson |
| D439,781 S | 4/2001 | Spore |
| 6,217,835 B1 | 4/2001 | Riley et al. |
| D441,861 S | 5/2001 | Hafliger |
| 6,233,773 B1 | 5/2001 | Karge et al. |
| 6,234,205 B1 | 5/2001 | D'Amelio et al. |

(56) References Cited

U.S. PATENT DOCUMENTS

| | | | |
|---|---|---|---|
| 6,237,178 B1 | 5/2001 | Krammer et al. | |
| 6,247,929 B1 * | 6/2001 | Bachman et al. | 433/80 |
| 6,293,792 B1 | 9/2001 | Hanson | |
| D449,884 S | 10/2001 | Tobin et al. | |
| 6,363,565 B1 | 4/2002 | Paffrath | |
| 6,468,482 B1 | 10/2002 | Frieze et al. | |
| 6,475,173 B1 | 11/2002 | Bachman et al. | |
| 6,485,451 B1 | 11/2002 | Roberts et al. | |
| 6,497,572 B2 | 12/2002 | Hood et al. | |
| 6,502,584 B1 | 1/2003 | Fordham | |
| D470,660 S | 2/2003 | Schaber | |
| 6,558,344 B2 | 5/2003 | McKinnon et al. | |
| 6,561,808 B2 | 5/2003 | Neuberger et al. | |
| D475,346 S | 6/2003 | McCurrach et al. | |
| 6,589,477 B1 | 7/2003 | Frieze et al. | |
| 6,602,071 B1 | 8/2003 | Ellion et al. | |
| 6,632,091 B1 | 10/2003 | Cise et al. | |
| D482,451 S | 11/2003 | Page et al. | |
| 6,640,999 B2 | 11/2003 | Peterson | |
| 6,647,577 B2 | 11/2003 | Tam | |
| 6,659,674 B2 | 12/2003 | Carlucci et al. | |
| 6,669,059 B2 | 12/2003 | Mehta | |
| D486,573 S | 2/2004 | Callaghan et al. | |
| 6,689,078 B1 | 2/2004 | Rehkemper et al. | |
| 6,699,208 B2 | 3/2004 | Bachman et al. | |
| 6,719,561 B2 | 4/2004 | Gugel et al. | |
| D489,183 S | 5/2004 | Akahori et al. | |
| 6,739,782 B1 | 5/2004 | Rehkemper et al. | |
| 6,740,053 B2 | 5/2004 | Kaplowitz | |
| D490,899 S | 6/2004 | Gagnon | |
| D491,728 S | 6/2004 | Jimenez | |
| D492,996 S | 7/2004 | Rehkemper et al. | |
| 6,761,324 B2 | 7/2004 | Chang | |
| 6,766,549 B2 | 7/2004 | Klupt | |
| D495,142 S | 8/2004 | Berde | |
| D495,143 S | 8/2004 | Berde | |
| 6,779,216 B2 | 8/2004 | Davies et al. | |
| 6,783,004 B1 | 8/2004 | Rinner | |
| 6,783,505 B1 | 8/2004 | Lai | |
| 6,796,796 B2 | 9/2004 | Segal | |
| 6,814,259 B1 | 11/2004 | Foster et al. | |
| D499,885 S | 12/2004 | Xi | |
| 6,835,181 B2 | 12/2004 | Hippensteel | |
| 6,884,069 B2 | 4/2005 | Goldman | |
| 6,907,879 B2 | 6/2005 | Drinan et al. | |
| D509,585 S | 9/2005 | Kling et al. | |
| D513,638 S | 1/2006 | Pan | |
| 7,080,980 B2 | 7/2006 | Klupt | |
| D530,010 S | 10/2006 | Luettgen et al. | |
| 7,117,555 B2 | 10/2006 | Fattori et al. | |
| D533,720 S | 12/2006 | Vu | |
| 7,147,468 B2 | 12/2006 | Snyder et al. | |
| D538,474 S | 3/2007 | Sheppard et al. | |
| D548,334 S | 8/2007 | Izumi | |
| D550,097 S | 9/2007 | Lepoitevin | |
| 7,276,035 B2 | 10/2007 | Lu | |
| 7,314,456 B2 | 1/2008 | Shaw | |
| D565,175 S | 3/2008 | Boyd et al. | |
| 7,344,510 B1 | 3/2008 | Yande | |
| 7,367,803 B2 | 5/2008 | Egeresi | |
| 7,455,521 B2 | 11/2008 | Fishburne, Jr. | |
| 7,469,440 B2 | 12/2008 | Boland et al. | |
| 7,500,584 B2 | 3/2009 | Schultz | |
| D601,697 S | 10/2009 | Sobiech et al. | |
| D603,708 S | 11/2009 | Handy | |
| 7,670,141 B2 | 3/2010 | Thomas et al. | |
| 7,677,888 B1 | 3/2010 | Halm | |
| 7,814,585 B1 | 10/2010 | Reich | |
| D629,884 S | 12/2010 | Stephens | |
| 7,862,536 B2 | 1/2011 | Chen et al. | |
| 7,878,403 B2 | 2/2011 | Hennick et al. | |
| 7,959,597 B2 | 6/2011 | Baker et al. | |
| 2003/0098249 A1 | 5/2003 | Rollock | |
| 2003/0204155 A1 | 10/2003 | Egeresi | |
| 2003/0213075 A1 | 11/2003 | Hui et al. | |
| 2004/0045107 A1 | 3/2004 | Egeresi | |
| 2004/0072122 A1 * | 4/2004 | Hegemann | 433/80 |
| 2004/0076921 A1 | 4/2004 | Gofman et al. | |
| 2004/0122377 A1 | 6/2004 | Fischer et al. | |
| 2004/0209222 A1 | 10/2004 | Snyder et al. | |
| 2005/0049620 A1 | 3/2005 | Chang | |
| 2005/0101894 A1 | 5/2005 | Hippensteel | |
| 2005/0271531 A1 | 12/2005 | Brown et al. | |
| 2006/0021165 A1 | 2/2006 | Boland et al. | |
| 2006/0026784 A1 | 2/2006 | Moskovich et al. | |
| 2006/0057539 A1 | 3/2006 | Sodo | |
| 2006/0078844 A1 | 4/2006 | Goldman et al. | |
| 2006/0079818 A1 | 4/2006 | Yande | |
| 2007/0082316 A1 | 4/2007 | Zhadanov et al. | |
| 2007/0105065 A1 | 5/2007 | Snyder et al. | |
| 2007/0113360 A1 | 5/2007 | Tsai | |
| 2007/0202459 A1 | 8/2007 | Boyd et al. | |
| 2007/0203439 A1 | 8/2007 | Boyd et al. | |
| 2007/0254260 A1 | 11/2007 | Alden | |
| 2009/0070949 A1 | 3/2009 | Sagel et al. | |
| 2009/0082706 A1 | 3/2009 | Shaw | |
| 2009/0124945 A1 | 5/2009 | Reich et al. | |
| 2009/0163839 A1 | 6/2009 | Alexander | |
| 2009/0281454 A1 | 11/2009 | Baker et al. | |
| 2010/0015566 A1 | 1/2010 | Shaw | |
| 2010/0190132 A1 | 7/2010 | Taylor et al. | |
| 2010/0209870 A1 | 8/2010 | Thomas et al. | |
| 2010/0239998 A1 | 9/2010 | Snyder et al. | |
| 2010/0261137 A1 | 10/2010 | Boyd et al. | |
| 2010/0266980 A1 | 10/2010 | Boyd et al. | |
| 2010/0326536 A1 | 12/2010 | Nan | |
| 2010/0330527 A1 | 12/2010 | Boyd et al. | |
| 2011/0027749 A1 | 2/2011 | Syed | |
| 2011/0097683 A1 | 4/2011 | Boyd et al. | |
| 2011/0139826 A1 | 6/2011 | Hair et al. | |
| 2011/0144588 A1 | 6/2011 | Taylor et al. | |
| 2011/0184341 A1 | 7/2011 | Baker et al. | |
| 2012/0021374 A1 | 1/2012 | Cacka et al. | |
| 2012/0045730 A1 | 2/2012 | Sayder et al. | |
| 2012/0077145 A1 | 3/2012 | Tsurukawa | |
| 2012/0141952 A1 | 6/2012 | Snyder et al. | |
| 2012/0277677 A1 | 11/2012 | Taylor et al. | |
| 2012/0277678 A1 | 11/2012 | Taylor et al. | |
| 2012/0295220 A1 | 11/2012 | Thomas et al. | |

FOREIGN PATENT DOCUMENTS

| | | |
|---|---|---|
| DE | 1466963 | 5/1969 |
| DE | 2409752 | 9/1975 |
| DE | 2545936 | 4/1977 |
| DE | 2910982 | 2/1980 |
| EP | 0023672 | 7/1980 |
| FR | 2556954 | 6/1985 |
| FR | 2654627 | 5/1991 |
| GB | 1182031 | 2/1970 |
| GB | 2018605 | 10/1979 |
| JP | 2-134150 | 4/1990 |
| JP | 2009-39455 | 2/2009 |
| WO | WO95/16404 | 6/1995 |
| WO | WO2004/021958 | 3/2004 |
| WO | WO2004/039205 | 5/2004 |

OTHER PUBLICATIONS

The Right Tool, Electron Fusion Devices, Inc., 2 pages, at least as early as Feb. 1991.

Japanese Packaging, 2 pages, at least as early as Dec. 2002.

Japanese Instruction Brochure, 2 pages, at least as early as Dec. 2002.

Brochure: Woog International, "You have a 98% chance of getting gum disease. Unless you read this.", Lancaster, Pennsylvania, Feb. 1987.

Brochure: Woog International, "We put the control of home dental care back into the hands of the professional", Lancaster, Pennsylvania, Feb. 1987.

Brochure: Woog International, "Products at a Glance: Home Dental Care System" Woog Orajet, at least as early as Dec. 18, 1998.

Website: http://www.just4teeth.com/product/Panasonic/Panasonic_Portable_Irrigator.htm, 2 pages, at least as early as Jun. 20, 2003.

(56) References Cited

OTHER PUBLICATIONS

Website: http://www.videodirectstore.com/store/merchant.mv?Screen=PROD&Product_Code=EW1'..., 2 pages, at least as early as Jun. 20, 2003.
Website: http://www.products.consumerguide.com/cp/family/review/index.dfm/id/18742, 2 pages, at least as early as Jun. 20, 2003.
Website: http://www.racekarteng.com/images/walbroparts.gif and http://www.muller.net/mullermachine/docs/walbro1.html, 4 pages, at least as early as Jun. 20, 2003.
European Search Report, EPO Application No. 07250799.9, Jul. 5, 2007.
European Examination Report, EPO Application No. 07250799.9, Feb. 5, 2009.
US RE27,274, 01/1972, Mattingly (withdrawn)

* cited by examiner

PUMP FOR DENTAL WATER JET

CROSS-REFERENCE TO RELATED APPLICATIONS

This application is a divisional of U.S. patent application Ser. No. 11/361,749 entitled "Water Jet Unit and Handle" filed on Feb. 24, 2006, which is hereby incorporated herein by reference in its entirety.

BACKGROUND a. Field of the Invention

The present invention relates generally to oral hygiene products, and more particularly to a dental water jet unit.

b. Background Art

Harmful bacteria often grows deep between teeth and below the gum line. Traditional toothbrush and flossing often cannot reach these areas to remove the bacteria and food debris from these areas. To overcome the limitations of toothbrushes and flossers, a dental water jet may provide a pressurized water stream to remove trapped debris and harmful bacteria from areas not easily reached by a toothbrush or flosser. Such a dental jet unit typically consists of a pump supplying pressurized water from a water reservoir to a tip. The tip has an opening that permits the pressurized water stream to be directed to the desired locations within the mouth.

However, in many such dental water jets, the reservoir holding the water to be pressurized and provided to the tip must be mated with a base of the water jet unit by inverting the reservoir and attaching the base thereto. This is typically so because the opening by which the reservoir is filled doubles as the opening through which water may exit the reservoir to be moved by the pump.

The pumps used in dental jet units for providing the necessary water pressures to effectively remove food debris and bacteria are often noisy. Although the noise does not affect the dental jet's effectiveness at removing food debris and bacteria, it is often unpleasant for the user.

Further, many dental water jets may not provide any visual indication when a tip is properly seated or mated with the dental water jet (typically within a handle). Similarly, many dental water jets may not visually indicate when the tip is properly removed. Thus, users of such dental water jets may not fully seat the tip, leading to ineffective or weakened oral irrigation. Additionally, the water may leak into the atmosphere between the interface of the improperly-seated tip and the handle. Further, users of such water jets may experience difficulty fully removing the tip from the handle.

Although some dental water jets permit a user to adjust the flow of fluid from the reservoir to the tip, many do not provide fine fluid flow control. Others have discrete settings as opposed to permitting a user to fine-tune fluid flow.

For these and other reasons, there is room in the art for an improved dental water jet.

SUMMARY

One embodiment of the present invention takes the form of an apparatus for providing a pressurized water stream for cleaning gums and teeth. The embodiment includes a base unit defining a cavity. The cavity contains a pump, which may move pressurized water from a reservoir to a tip in fluid communication with the pump. The reservoir may be supported on the base unit and in fluid communication with the pump. The pump may be connected to an electrical power source in order to power the pump. The pump may be turned on and off using a switch. A flow control knob may be turned to selectively adjust the water pressure supplied by the tip between a minimum and a maximum value. The reservoir may be removed from the base unit so that it may be filled with a fluid, such as water, from a fluid source (such as a water faucet). The reservoir may support a container for storing tips or other items.

Fluid may flow from the reservoir, through the base supporting the reservoir, along a tube, from the tube into the handle, and into the tip. The fluid may be propelled by a motive source, such as a piston, to facilitate this flow. Fluid may ultimately be ejected from the tip and into the mouth of a user (for example) to provide oral irrigation and/or cleaning of the teeth, gums, and tongue.

One embodiment of the present invention takes the form of an apparatus for adjusting a fluid pressure supplied by a pump to a tip, including a pump body defining a fluid chamber, a flow control rotatably connected to the pump body, a flow regulation conduit at least partially defined by the flow control, a bypass valve in fluid communication with the fluid chamber and the flow regulation conduit, and a fluid passage between the fluid chamber and the tip. In such an embodiment, the pump body and the flow control together define a return channel in fluid communication with the flow regulation conduit. Further, the depth of the fluid regulation conduit proximate the bypass valve may be varied by selectively moving the flow control relative to the pump body. Additionally, varying the depth of the fluid regulation conduit varies a fluid pressure within the fluid passage.

Another embodiment of the present invention takes the form of a dental water jet unit including a base unit defining a cavity, a reservoir in fluid communication with a pump contained within the cavity and connected to the base unit by at least one vibration reduction mount, and a tip operative to deliver a stream of pressurized fluid and in fluid communication with the pump.

Yet another embodiment of the present invention takes the form of a container for storing items, including a container base including a surface operative to be received within a reservoir, a lid connected to and movable relative to the container base, at least one first aperture defined on the container base, and at least one second aperture defined on the lid, wherein the container base and the lid define for at least one movable position a substantially enclosed volume for storing at least one item.

Still another embodiment of the present invention is a dental water jet handle including a housing defining a cavity, a tip attachment mechanism operationally attached to the housing, a visual indicator operationally attached to the housing, the visual indicator visually indicating when the tip is attached to the housing and further visually indicating when the tip is detached from the housing, a pause button, and a stop plunger attached to the pause button and at least partially received within the cavity. In such an embodiment, depressing the pause button halts a fluid flow through the cavity and to the tip. Additionally, an audible indication that the tip is properly attached may be provided. For example, a click, bell or whistle may be heard when the tip is seated. The audible indication may be mechanically or electronically generated.

A further embodiment of the present invention takes the form of a dental water jet unit including a base unit defining a cavity, a plurality of footings attached to the base unit and operative to elevate the base unit above a surface supporting the base unit, a reservoir in fluid communication with a pump contained within the cavity, and a tip operative to deliver a stream of pressurized fluid and in fluid communication with the pump.

Yet a further embodiment of the present invention takes the form of a dental water jet unit pump including a pump chassis, an eccentric end plate movably connected to the pump chassis, a first alignment shaft connected to the pump chassis, a second alignment shaft connected to the eccentric end plate, a first gear rotating around a longitudinal axis of the first alignment shaft, and a second gear engaging the first gear and rotating around a longitudinal axis of the second alignment shaft. In such an embodiment, selectively moving the eccentric end plate relative to the pump chassis selectively moves the second gear relative to the first gear.

Still a further embodiment of the present invention takes the form of a dental water jet unit including a base unit defining a cavity, a reservoir in fluid communication with a pump contained within the cavity, a tip in fluid communication with the pump, and a reed valve located within the base unit. In such an embodiment, the reed valve regulates a flow of a fluid from the pump to the tip. Further, the reed valve prevents the fluid from flowing from the tip to the pump.

An additional embodiment of the present invention takes the form of a dental water jet unit including a base unit having a basin for receiving a reservoir, a reservoir valve initially biased to a closed position and operationally attached to the reservoir, and a tube projection connected to the base unit and opening the valve when the reservoir is received within the basin. In such an embodiment, the basin and the reservoir are configured to guide the reservoir valve adjacent to the tube projection.

These and additional embodiments, features, and operations of the invention will be apparent to those skilled in the art upon reading the following disclosure.

DETAILED DESCRIPTION OF THE INVENTION

One embodiment of the present invention takes the form of an apparatus for providing a pressurized water stream for cleaning gums and teeth. The embodiment includes a base unit defining a cavity. The cavity contains a pump, which may move pressurized water from a reservoir to a tip in fluid communication with the pump. The reservoir may be supported on the base unit and in fluid communication with the pump. The pump may be connected to an electrical power source in order to power the pump. The pump may be turned on and off using a switch. A flow control knob may be turned to selectively adjust the water pressure supplied by the tip between a minimum and a maximum value. The reservoir may be removed from the base unit so that it may be filled with a fluid, such as water, from a fluid source (such as a water faucet). The reservoir may support a container for storing tips or other items.

Fluid may flow from the reservoir, through the base supporting the reservoir, along a tube, from the tube into the handle, and into the tip. The fluid may be propelled by a motive source, such as a piston, to facilitate this flow. Fluid may ultimately be ejected from the tip and into the mouth of a user (for example) to provide oral irrigation and/or cleaning of the teeth, gums, and tongue.

Figure 1:
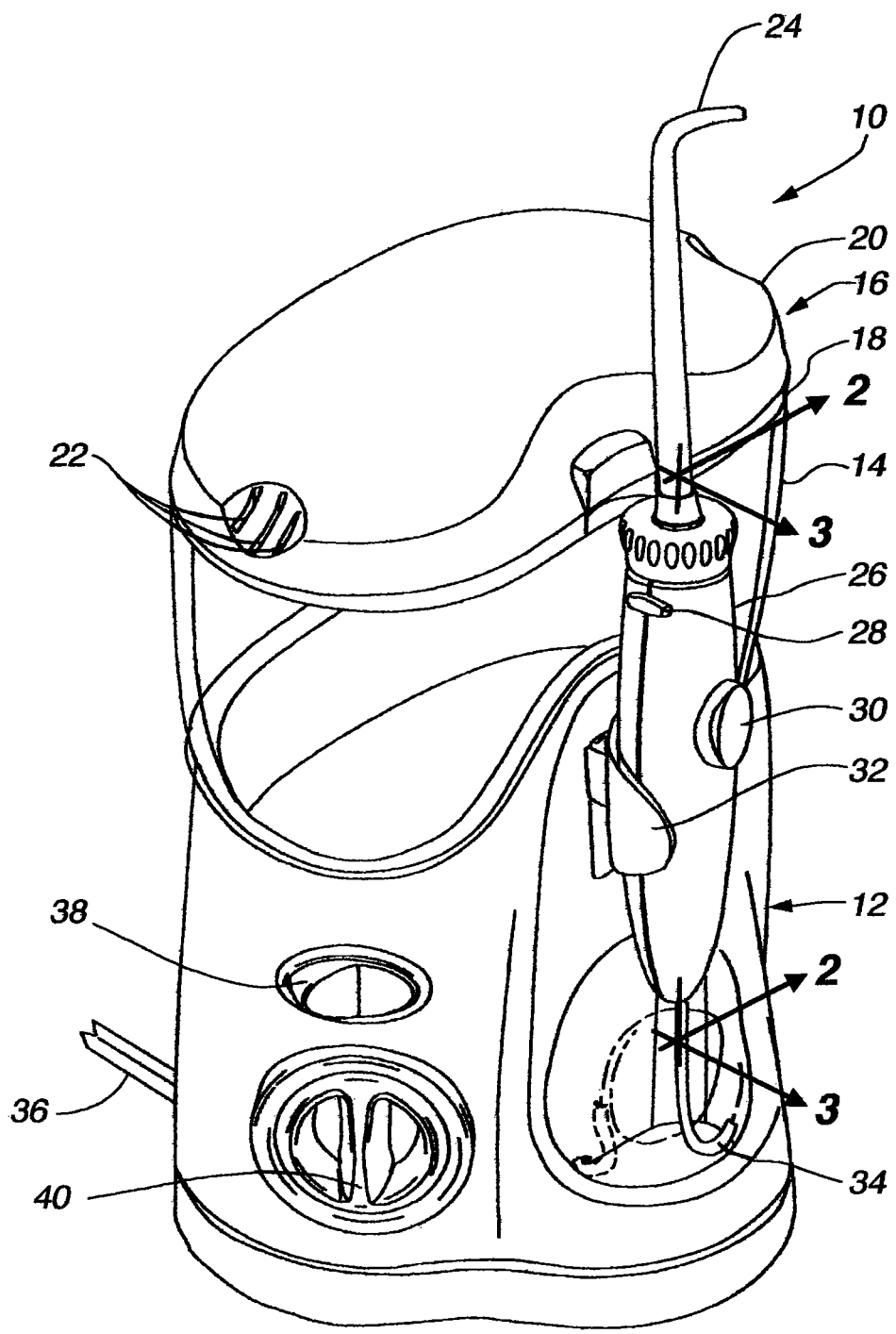
FIG. 1 depicts a perspective view of a first embodiment of an apparatus for providing a pressurized fluid stream.

FIG. 1 depicts a perspective view of a first embodiment of a dental water jet apparatus 10 for providing a pressurized fluid stream. The embodiment may include a base unit 12, which may support a reservoir 14 for storing a fluid such as water. A container 16 having a container base 18 and a lid 20 may be positioned atop the reservoir 14 and define one or more ventilation holes 22. The container 16 may be used for storing items, including accessories utilized with the apparatus 10. One exemplary accessory is a tip 24 having an opening for delivering a pressurized fluid stream. Such a tip 24 may be attached to a handle 26 having a latch 28 that selectively detaches the tip 24 from the handle 26. The handle 26 may further include a button 30 for pausing fluid flow to the tip 24. The handle 26 may be removably secured to the base unit 12 via a clamp 32 joined to the base unit 12 and may be coupled to a tube 34 in fluid communication with a pump contained within the base unit 12. A power cord 36 may connect a power source (not shown) to the pump. A switch 38 may be connected to the base unit 12 for turning the pump on and off.

Additional controls may be used beyond the aforementioned switch 38. For example, a knob 40 may be connected to the pump for adjusting the fluid pressure of a fluid supplied by the pump. The knob 40 may be, for example, inserted through a knob aperture in the base unit 12 in order to be accessible to an operator. Each of the base unit 12, reservoir 14, container 16, tip 24, handle 26, clamp 32, tube 34, switch 38, and knob 40 may be composed of plastic, metal, rubber, carbon composites, another suitable material, or some combination thereof.

Figure 2:
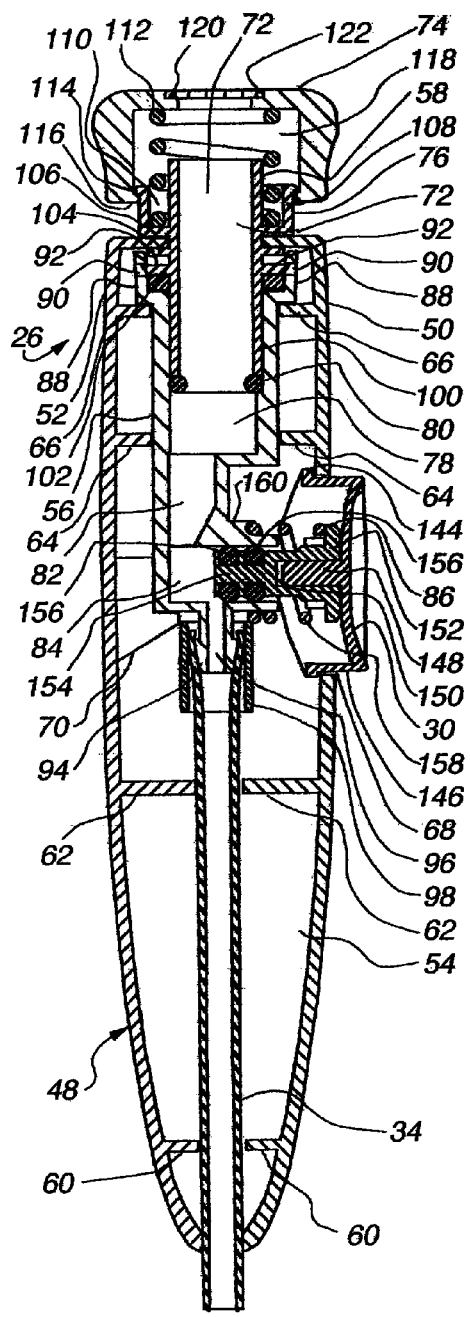
FIG. 2 depicts a cross-sectional view of the handle depicted in FIG. 1, viewed along line 2-2 in FIG. 1.
Figure 3:
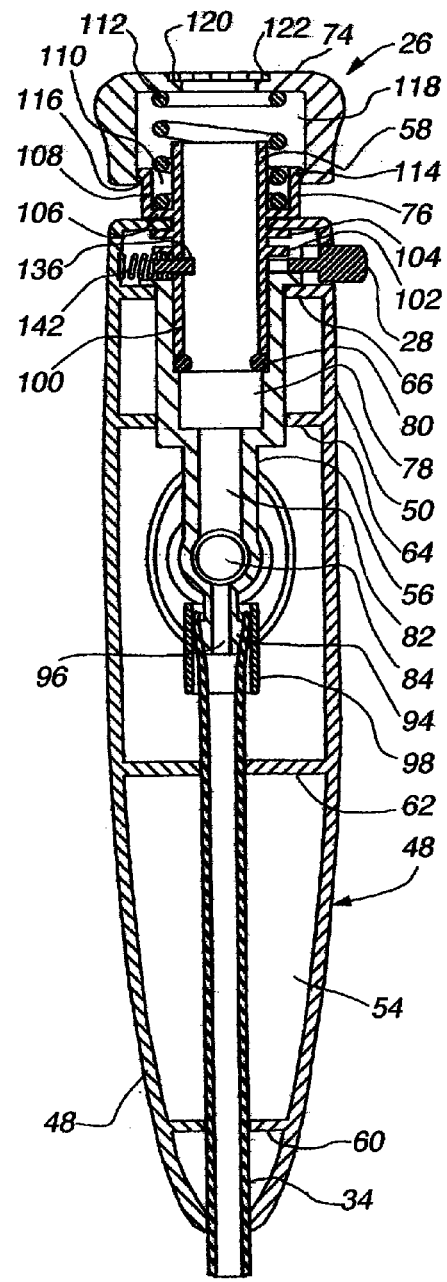
FIG. 3 depicts a cross-sectional view of the handle depicted in FIG. 1, viewed along line 3-3 in FIG. 1.

FIG. 2 depicts a cross-sectional view of the handle 26 viewed along line 2-2 in FIG. 1, while FIG. 3 depicts a cross-sectional view of the handle 26 viewed along line 3-3 in FIG. 1. With reference to these figures, the handle 26 may include a handle housing 48 composed of a first housing segment 50 and a second housing segment 52. The first and second handle housing segments 50, 52 together define a cavity 54 in which a valve body 56, the tube 34, and a collar unit 58 may reside. The first and second handle housing segments 50, 52 may each include first, second, third, and fourth interior walls 60, 62, 64, 66 for aligning the valve body 56, the tube 34, and the collar unit 58 within the cavity 54. The interior walls 60, 62, 64, 66 generally extend in a horizontal plane with respect to the handle 26, and inwardly from one of the first and second housing segments 50, 52. Each interior wall 60, 62, 64, 66 may align with a mating interior wall extending from the opposing housing segment when the handle 26 is assembled.

The first handle housing segment 50 may include a button aperture 68 receiving the button 30. Similarly, the second handle housing segment 52 may include one or more L-shaped sidewalls 70 that support the valve body 56 when the button 30 is pressed. Generally, pressing the button 30 forces the valve body 56 against the L-shaped sidewall 70.

The valve body 56 may define a series of fluid passages along its length. In particular, an inner surface of the valve body 56 may define a valve body aperture for receiving a collar unit 58 defining a first fluid passage 72 or conduit extending from the first and second handle housing segments 50, 52 to a handle head 74 formed at the top of the handle 26. (As explained below, the handle head 74 generally receives the tip 24.) The collar unit 58 may include a collar 76 that may encircle at least a portion of the first fluid passage 72.

Additionally, the inner surface of the valve body 56 may be stepped to define a second fluid passage 78 or conduit adjacent to the first fluid passage 72. This second fluid passage 78 typically has a cross-sectional area at least slightly smaller in at least one dimension than the cross-sectional area of the first fluid passage 72. This change in the cross-sectional area forms a step. The step may support a valve body O-ring 80, which may prevent pressurized fluid from leaking into the handle housing 48 along the joint formed between the valve body 56 and the collar unit 58.

The inner surface of the valve body 56 may be stepped again to define a third fluid passage 82 or conduit adjacent to the second fluid passage 78 having a cross-sectional area smaller in at least one dimension than the cross-sectional area of the second fluid passage 78. The inner surface of the valve body 56 also may define a fourth fluid passage 84 or conduit. This fourth fluid passage 84 may be generally transverse to the first, second, and fluid passages 72, 78, 82. That is, while the first, second and third fluid passages 72, 78, 82 extend along the longitudinal axis of the handle 26, the fourth fluid passage 84 extends along the transverse axis of the handle 26. The fourth fluid passage 84 generally underlies the button 30 and may receive a stop plunger 86. The third fluid passage 82 provides a fluid connection between the second 72 and fourth fluid passages 78, 84, while the fourth fluid passage 84 receives the stop plunger 86 for pausing the flow of fluid from the tube 34 to the tip 24 as described in more detail below.

At a first end of the valve body 56 (i.e., the end of the valve body 56 wherein the first fluid passage 72 is formed), a pair of tab walls 88 may extend from the valve body 56 in a direction generally parallel to the longitudinal axis of the handle 26. Each tab wall 88 may include a tab aperture 90 sized to receive a tab 92 associated with, or placed on, the collar unit 58. At a second end of the valve body 56 (i.e., the end of the valve body 56 adjacent the fourth fluid passage 84), an arrowhead-shaped wall 94 for receiving the tube 34 may extend from the valve body 56 in a direction generally aligned with the handle's 26 longitudinal axis. When joined to the valve body 56 by the arrowhead shaped wall 94, the tube 34 may fluidly communicate with the fourth fluid passage 84 via an opening 96 in the arrow-head shaped wall 94. A tube clamp 98 may clamp the portion of the tube's 34 inner surface received by the arrowhead shaped wall 94 against the arrowhead shaped wall's 94 outer surface.

The first fluid passage 72 may extend through the collar unit 58 and into the handle head 74. The collar unit wall 100 (or walls, in some embodiments) of the first fluid passage 72 may have first, second, and third collar unit projections 102, 104, 106 extending from its outer surface. The first collar unit projection 102 may include one or more of the aforementioned tabs 92 for connecting the collar unit 58 to the valve body 56 when a portion of the collar unit 58 is received within the valve body 56. As the collar unit 58 is received within the valve body 56, the tabs 92 push the tab walls 88 outwardly until the tabs 92 generally align with the tab apertures 90. Once aligned, the tabs 92 are received with the tab apertures 90, thereby allowing the tab walls 88 to return to their original position, and thus retain the tabs 92 within the tab apertures 90. Retention of the tabs 92 within the tab apertures 90 results in the collar unit 58 and the valve body 56 being connected. The second collar unit projection 104 may align the collar unit 58 with the first and second handle housing segments 50, 52. The collar 76 may be composed of the third collar unit projection 106 and a collar sidewall 108 extending from the free end of the third collar unit projection 106 in a direction generally parallel to the longitudinal axis of the handle 26, thereby defining a space 110 between the between the collar sidewall 108 and the outer surface of the collar unit wall 100.

A first spring 112 may be located within the space 110 to maintain a pre-determined distance between a handle head 74 and the handle housing 48 as described in more detail below. A fourth collar unit projection 114 may extend generally transversely from the free end of the collar sidewall 108, thereby providing a surface for engaging handle head flanges 116 extending inwardly from an inner surface of the handle head 74.

The inner surface of the handle head 74 may define a handle head space 118 receiving the first spring 112. The first spring 112 may compress to engage the third collar unit projection 106 and the handle head's 74 inner surface when the handle head 74 and collar unit 58 are joined. The first spring 112 may exert an upward force against the handle head 74 when compressed. Although this upward force may tend to drive the handle head 74 away from the collar unit 58, engagement between the handle head flanges 116 and the fourth collar unit projection 114 will resist separation of the handle head 74 and collar unit 58 by this upward force. Further, the cumulative effect of the upward force by the first spring 112 being resisted by the engagement between the head handle flanges 116 and the fourth collar unit projection 114 is that the handle head 74 generally will be maintained at a pre-determined distance from the third collar unit projection 106 of the collar unit 58. Thus, when the joined collar unit 58 and handle head 74 are positioned adjacent to the handle housing 48, the handle head 74 will generally be maintained at a pre-determined distance from the handle housing 48 as shown in FIGS. 2 and 3.

Figure 4:
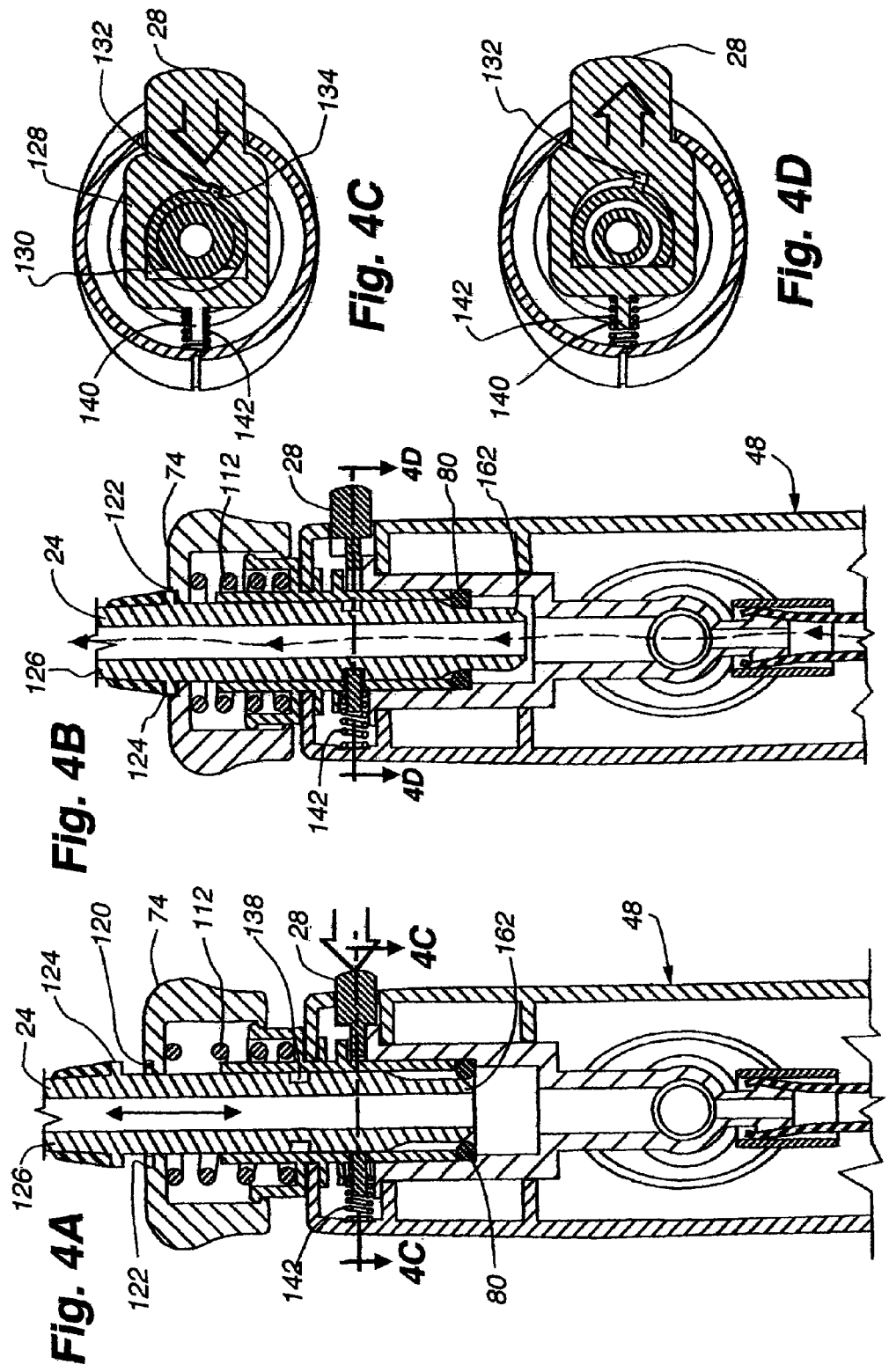
FIG. 4A depicts a portion of the cross-sectional view of the handle shown in FIG. 3 showing a tip being inserted or removed from the handle.
FIG. 4B depicts a portion of the cross-sectional view of the handle shown in FIG. 3 showing a tip coupled to the handle.
FIG. 4C depicts a cross-sectional view of the handle and tip shown in FIG. 4A, viewed along line 4C-4C in FIG. 4A.
FIG. 4D depicts a cross-sectional view of the handle and tip shown in FIG. 4B, viewed along line 4D-4D in FIG. 4B.

As shown in FIG. 4B, the handle head 74 may be depressed to be adjacent the handle housing 48. Further, when the handle head 74 is positioned adjacent the handle housing 48, the handle head 74 may be rotated relative to the collar unit 58 around a longitudinal axis of the handle 26 since the handle head 74 is not fixedly connected to the collar unit 58. As described in more detail below, a tip 24 received within the handle head 74 may be rotated around the longitudinal axis of the handle 26 by rotating the handle head 74 around this longitudinal axis, thereby permitting the direction of the fluid stream exiting the tip 24 to be changed by rotating the handle head 74.

The handle head 74 may be depressed into the position shown in FIG. 4B when a tip 24 is received within the handle head's 74 opening and coupled with the latch 28 as described in more detail below. As the handle head 74 is depressed towards the handle housing 48, the first spring 112 compresses further. The further compressed first spring 112 will exert an upward force, which will return the handle head 74 back to its original pre-determined distance from the handle housing 48 in the absence of another force opposing this upward force. When the tip 24 is coupled with the latch 28 as described in more detail below, this upward force will be opposed, thereby maintaining the handle head 74 in a position adjacent the handle housing 48 as shown in FIG. 4B. When the tip 24 is decoupled from the latch 28, the force opposing the upward force exerted by the first spring 112 is removed, thereby allowing the first spring 112 to move the handle head 74 back to its original position as shown in FIGS. 2 and 3. This movement of the handle head 74 from a position adjacent the handle housing 48 to its pre-determined position from the handle housing 48 provides a visual indication that the tip 24 is decoupled from the latch 28.

The handle head 74 may include a recessed surface 120 encompassing an opening adapted to receive the tip 24 and surrounded by a recessed wall 122. With reference to FIGS. 4A and 4B, the recessed wall 122 may define a shape adapted to mate with a tip annular ring 124 extending from an exterior surface of a portion of the tip 24, namely a tip shaft 126. The engagement of the recessed wall 122 with the tip annular ring 124 may permit the tip 24 to be rotated around a longitudinal axis of the handle 26 as the handle head 74 rotates around the longitudinal axis of the handle 26.

As mentioned above, the latch 28 may permit the tip 24 to be selectively attached or detached from the handle 26, and specifically from the handle head 74. The operation of the latch 28 will now be described. With reference to FIGS. 2, 3, 4A, 4B, 4C and 4D, the latch 28 may have a latch body 128 defining a latch aperture 130 that may be received on the collar unit wall 100. As shown in FIG. 4C, a latch slot 132 may extend from the latch aperture 130 and mate with a collar tongue 134 extending from the collar unit wall 100, thereby providing an alignment mechanism for properly aligning the latch 28 relative to the collar unit 58 when joining the latch 28 and the collar unit 58 as described in more detail below. A portion of the latch body 128 may be received within a collar opening 136 in the collar unit wall 100. As described in more detail below, this portion of the latch body 128 may mate with a groove 138 in the tip 24, thereby retaining the tip 24 when it is engaged with the handle 26. A latch stub 140 may extend from the latch body 128 and receive a second spring 142. When the handle 26 is assembled, the second spring 142 will be compressed between the latch body 128 and the handle housing 48 as shown in FIG. 3. The compressed second spring 142 will exert a force upon the latch 28 that pushes a portion of the latch body 128 into the collar opening 136 as shown in FIG. 3 when a tip 24 is not received within the first fluid passage 72. As described in more detail below, when a tip 24 is received within the first fluid passage 72, the second spring 142 also pushes a portion of the latch body 128 into the tip groove 138, thereby coupling the tip 24 with the latch 28.

Figure 5:
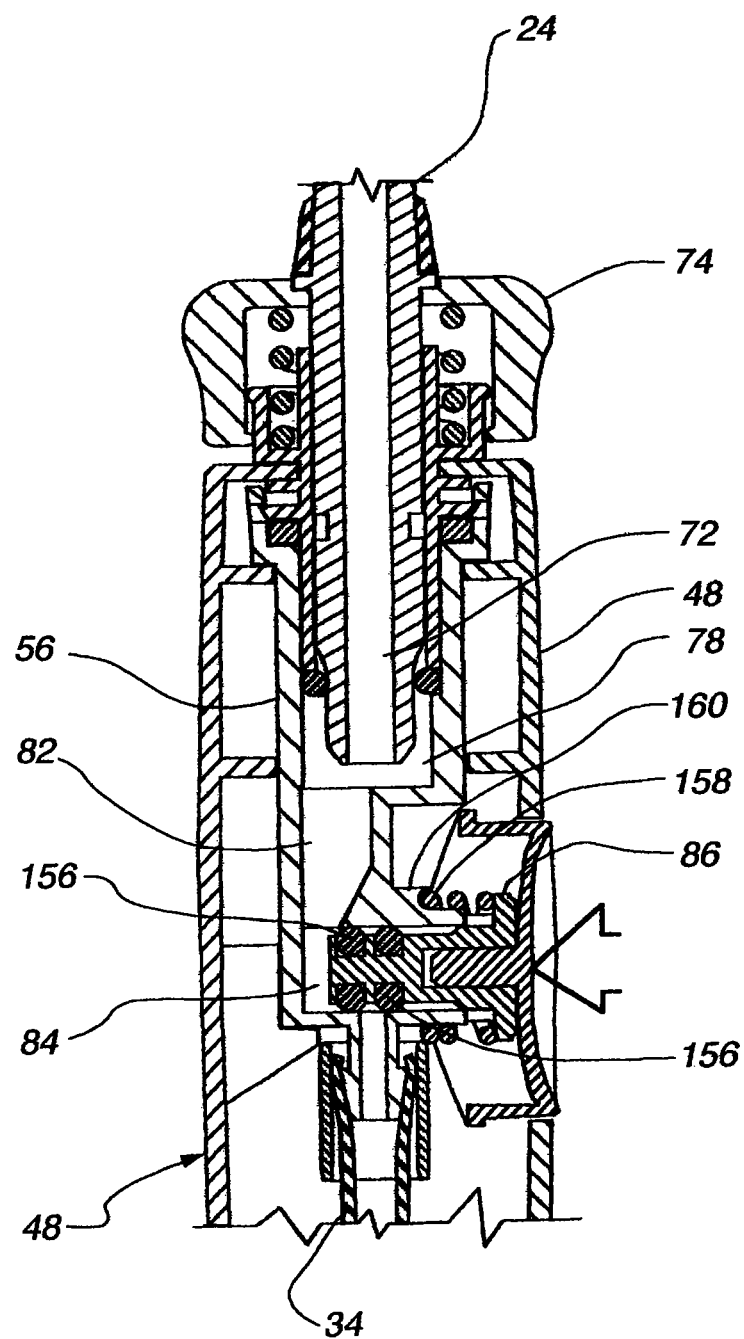
FIG. 5 depicts a portion of the cross-sectional view of the handle shown in FIG. 2, showing a tip attached to the handle and the handle's button pressed to pause the flow of fluid from the tube to the tip.

Returning to FIGS. 2 and 3, the button 30 may be received within the button aperture 68 of the first handle housing segment 50. The button 30 may include a generally concave and ovoid first surface. A lip 144 or other projection extending from a wall 146 of the button 30 generally may prevent the button 30 from passing entirely through the button aperture 68 when the button 30 is received therein. The button 30 may include a stop plunger projection 148 adapted to mate with a stop plunger aperture 150 defined by a stop plunger body 152 to connect the button 30 to the stop plunger 86. A glue, epoxy, or other adhesive may also be used to join the stop plunger 86 to the button 30. The stop plunger 86 may further include a stop plunger shaft 154 extending from the stop plunger body 152. The stop plunger shaft 154 may include one or more stop plunger grooves that each may receive a stop plunger O-ring 156. The stop plunger O-rings 156 may prevent a fluid from leaking into the handle housing 48 of the handle 26 through the joint formed by the stop plunger 86 and the valve body 56. The stop plunger O-rings 156 may also prevent fluid from the leaking into the first fluid passage 72, or into the handle housing 48 of the handle 26, when the stop plunger 86 is engaged to stop the flow of fluid through the valve body 56 as shown in FIG. 5. When the stop plunger 86 is in this closed position, the stop plunger 86 seats within the fourth fluid passage 84, thereby preventing fluid flow from the tube 34 through the fourth fluid passage 84 and, ultimately, through the valve body 56. This, in turn, prevents fluid from flowing into the first fluid passage 72 and any tip 24 connected to the handle head 74.

A third spring 158 may be located between the stop plunger 86 and one or more spring-engaging protrusions 160 formed in the valve body 56. The third spring 158 is biased to return the stop plunger 86 to an open position when the button 30 is released. When the stop plunger 86 is in the open position, fluid may flow through the tube 34, into the valve body 56, and into a tip 24 connected to the handle head 74. Fluid flow through the present embodiment is described in more detail below.

With reference to FIGS. 4A and 4B, the operation of attaching and detaching a tip 24 from the handle 26 will be described. A tip proximal end 162 is inserted into the first fluid passage 72 (the fluid passage through the collar unit 58) through the opening in the handle head 74. As the tip 24 is inserted, the portion of the latch body 128 received within the collar opening 136 in the collar unit wall 100 engages the tip proximal end 162. This engagement causes the latch body 128 to slide along the sloped surface of the tip proximal end 162, thereby pushing the latch body 128 out of the collar opening 136. As the latch body 128 is pushed out of the collar opening 136, the second spring 142 is compressed between the latch 28 and the handle housing 48 (see FIG. 4A). As the tip 24 continues to be inserted within the first fluid passage 72, the tip annular ring 124 formed on the tip exterior engages the handle head's recessed surface 120. Accordingly, as the tip 24 is pushed, the handle head 74 likewise moves towards the handle housing 48. As the handle head 74 moves towards the handle housing 48, the first spring 112 compresses between the handle head 74 and the collar unit 58.

As the tip proximal end 162 approaches the third fluid passage 82 formed in the valve body 56, the tip groove 138 generally aligns with the latch body 128 and collar opening 136 as shown in FIG. 4B. When the latch body 128 is aligned with the tip groove 138 and collar opening 136, the compressed second spring 142 pushes a portion of the latch body 128 into the collar opening 136 and the tip groove 138. Receipt of a portion of the latch body 128 within the tip groove 136 couples the tip 24 with the latch 28 thereby attaching the tip 24 to the handle 26. A noise may occur when the latch body 128 is received within the tip groove 138, thereby providing an audible indication that the tip 24 is attached to the handle 26. The noise may be a click, beep, bell, whistle, and so forth. The noise may be mechanically produced (for example, a click resulting from a portion of the tip 24 impacting a portion of the handle 26, or a click resulting from a portion of the tip 24 springing outward or mechanically deforming). Alternatively, the noise may be electronically produced (such as a beep or chime from an electronic speaker activated when the tip 24 is properly seated). A segment of the tip 24 may, for example, mechanically depress an electronic element to initiate the noise, or may complete an electronic circuit. Likewise, the latch body 128 may mechanically depress an electronic element associated with the tip 24 (such as within the tip groove 138) or complete an electronic circuit with the tip 24 when seated in the tip groove 138.

To detach the tip 24 from the handle 26, the latch 28 is pressed towards the handle 26. When the latch 28 is pressed, the portion of the latch body 128 received within the tip groove 138 moves out of the tip groove 138. Once no portion of the latch body 128 remains within the tip groove 138, the first spring 112 expands. As the first spring 112 expands, the handle head 74 moves away from the handle housing 48, thereby returning the handle head 74 to the position occupied prior to insertion of the tip 24. This motion also forces the tip 24 upward. As the tip 24 moves upward, the tip groove 138 moves upward, and thus is no longer aligned with the latch body 128. Once the tip groove 138 ceases to be aligned with the latch body 128, the tip 24 may be removed from the handle 26 since it is no longer coupled to the handle 26 by the latch 28. The handle head's return towards its original position prior to insertion of the tip 24 provides a visual indication that the tip 24 is no longer coupled to the handle 26 by the latch 28. More particularly, in addition to the motion of the handle head 74, the collar unit 58 appears to expand as the handle head 74 retreats from the handle 26 in order to provide the aforementioned visual indication.

Figure 6:
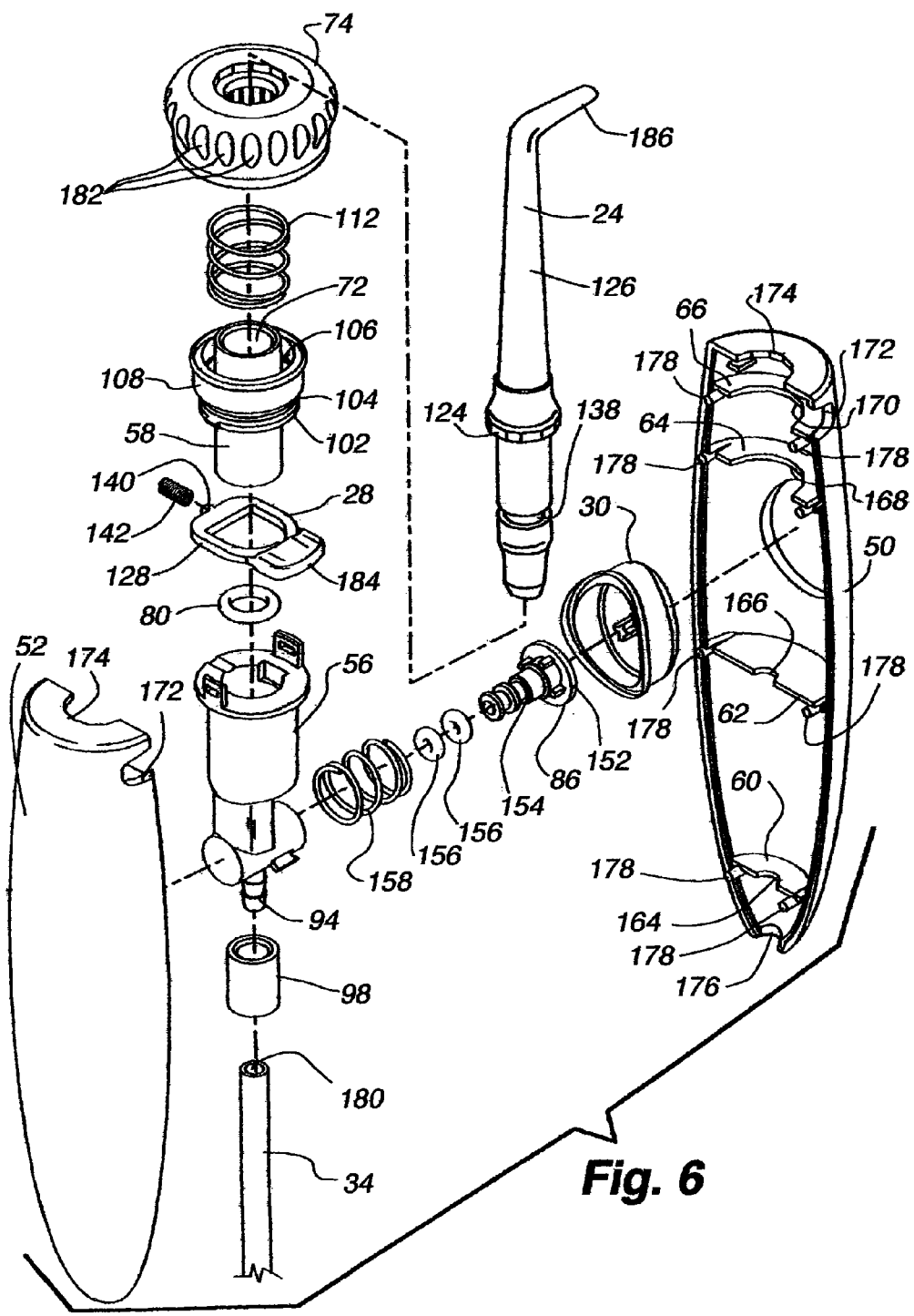
FIG. 6 depicts an exploded perspective view of the handle depicted in FIG. 1.

FIG. 6 depicts an exploded perspective view of various components of the embodiment of the handle 26 depicted in FIGS. 2, 3, 4A, 4B, and 5. The components of the embodiment may include the first and second handle housing segments 50, 52, the tube 34, the latch 28, the button 30, the handle head 74, the collar unit 58, the valve body 56, the tube clamp 98, the stop plunger 86, the valve body and stop plunger O-rings 80, 156, and the first, second and third springs 112, 142, 158. The first and second handle housing segments 50, 52 may separate in order to receive the collar unit 58, the latch 28, the body valve 56, the stop plunger 86, the button 30, the second and third springs 142, 158, the tube clamp 98, a portion of the tube 34, and the valve body and stop plunger O-rings 80, 156.

Semicircular first, second, third and fourth notches 164, 166, 168, 170 formed in each of the first, second, third and fourth interior walls 60, 62, 64, 66 extending from the first and second handle housing segments 50, 52 cooperate to form first, second, third, and fourth handle housing apertures, respectively. When the first, second, third and fourth interior walls 60, 62, 64, 66 of the first handle housing segment 50 abut the first, second, third, and fourth interior walls 60, 62, 64, 66 of the second handle housing segment 52, the semicircular notches 164, 166, 168, 170 in each such interior wall align with the corresponding notches formed in the mating interior wall. Thus, each of the aforementioned handle housing apertures are generally circular in shape, although in alternative embodiments the handle housing apertures may be of any desired shape.

The first, second, third, and fourth interior walls 60, 62, 64, 66 extending from the interior surfaces of the handle housing segments 50, 52 may each have a length generally parallel to the lengths of the other interior walls. The interior walls 60, 62, 64, 66 may generally be located along the lengths of their respective handle housing segments 50, 52 such that when the first and second handle housing segments 50, 52 are joined, the notches 164, 166 in the first and second interior walls 60, 62 define a pair of co-axially aligned first and second handle housing apertures that may receive the tube 34, and the notches 168, 170 in the third and fourth interior walls 64, 66 define a pair of coaxially aligned third and fourth handle housing apertures that may receive the valve body 56.

Semicircular fifth, sixth, and seventh notches 172, 174, 176 formed in each of the exterior walls of the first and second handle housing segments 50, 52 cooperate to form fifth, sixth and seventh handle housing apertures, respectively. When the first and second handle housing segments 50, 52 are joined, the semicircular notches 172, 174, 176 in each exterior wall of the handle housing segments 50, 52 align with the corresponding notches formed in the mating exterior wall. Thus, each of the aforementioned fifth, sixth, and seventh handle housing apertures are generally circular in shape, although in alternative embodiments the handle housing apertures may be of any desired shape. Further, when the first and second handle housing segments 50, 52 are joined, the fifth handle housing aperture may receive the latch 28, the sixth handle housing aperture may receive the collar unit 58, and the seventh handle housing aperture may receive the tube 34. One or more pegs 178 may extend from the interior surface of the first handle housing segment 50 proximate the first, second, third, and fourth interior walls 60, 62, 64, 66. Each peg 178 may be adapted to mate with a corresponding hole in the second handle housing segment 52. The pegs 178 and the holes may be dimensioned such that each peg 178 will relatively snugly fit within its corresponding hole. The friction resulting from this fit may resist decoupling of the handle housing segments 50, 52. Alternatively and/or additionally, the first and second housing segments 50, 52 may be joined using glue, epoxy, fasteners, sonic welding, any other known method for joining two items, or by a combination of known methods. For example, the pegs 178 may be glued or adhered within the holes.

Still with respect to FIG. 6, an interior fluid passage 180 may be formed within the hollow tube 34. At a first end, the interior passage 180 may be dimensioned so that an end portion of the tube 34 may be received on the arrowhead wall 94 of the valve body 56. The tube clamp 98 may be a generally cylindrical and likewise hollow. The tube clamp 98 may be slid over the exterior surface of the tube 34.

The handle head 74 may include a generally crown-shaped upper surface with one or more recesses 182. A user may rest his or her fingers on or in these recesses 182 to grip the handle head 74 when rotating it around the handle's 26 longitudinal axis. The first fluid passage 72 is generally cylindrical. The first, second, and third collar unit projections 102, 104, 106 may be generally annular, and the collar sidewall 108 may be generally annular.

The latch 28 may be composed of a latch key 184, the latch body 128, and the latch stub 140. The latch key 184 may be a pentagonal structure. The latch body and stub 128, 140 may each be a rectangular solid. The latch aperture 130 defined within the latch body 128 may be generally arch-shaped with the straight edge of the arch being partially received within the collar opening 136 located in the collar unit wall 100. The stop plunger 86 may form an at least partially-circular plane with a cylindrical shaft 154 extending transversely from the planar body 152.

The tip 24 may include an elongated, generally cylindrical shaft 126 that is bent or angled at a distal end 186. The inner surface of the tip shaft 126 may define a tip fluid passage, which may narrow along the tip shaft's length or at least near the distal end 186. The tip shaft 126 may include the tip groove 138, which may engage the latch 28 as described above, and the tip annular ring 124, which may extend around the tip shaft's circumference and engage the handle head 74 as described above.

A method for assembling the handle 26 will now be described. The first spring 112 is received within the annular space 110 defined by the collar sidewall 108 and collar unit wall 100. The handle head 74 is pressed onto the collar unit 58 until its flanges 116 clear the fourth collar unit projection 114 extending from the collar sidewall 108. Thus, when attempting to separate the handle head 74 from the collar unit 58, the handle head flanges 116 will abut the fourth collar unit projection 114 and prevent disconnection. The collar unit wall 100 is inserted through the latch aperture 130 until a surface of the latch body 128 abuts the first collar unit projection 102. The second spring 142 is received on the latch stub 140. The valve body O-ring 80 is positioned at the end of the first fluid passage 72 opposite the collar unit 58, and the collar unit wall 100 is inserted into the valve body aperture of the valve body 56 until the tabs 92 of the collar unit 58 engage the tab apertures 90 defined in the tab walls 88 of the valve body 56.

The third spring 158 is placed against the valve body 56 and contacts the spring-engaging protrusions 160 of the valve body 56. The stop plunger O-rings 156 placed about the stop plunger 86 are received within the stop plunger grooves, and the stop plunger 86 is connected to the button 30 and inserted at least partially into the fourth fluid passage 84. The tube 34 is received on the arrowhead wall 94 extending from the valve body 56 and the tube clamp 98 is slid onto the portion of the tube 34 received by the arrowhead wall 94. The valve body 56 (with attached components) is placed within the second handle housing segment 52; the first, second, third, and fourth interior walls 60, 62, 64, 66 facilitate locating the valve body 56 and attached components within the second handle housing segment 52. Next, the first handle housing segment 50 may be joined with the second handle housing segment.

The previously described method is merely one exemplary method of assembly. Accordingly, other methods of assembling the handle 26 may be used, including, without limitation, varying the order of some or all of the operations described above.

Figure 7:
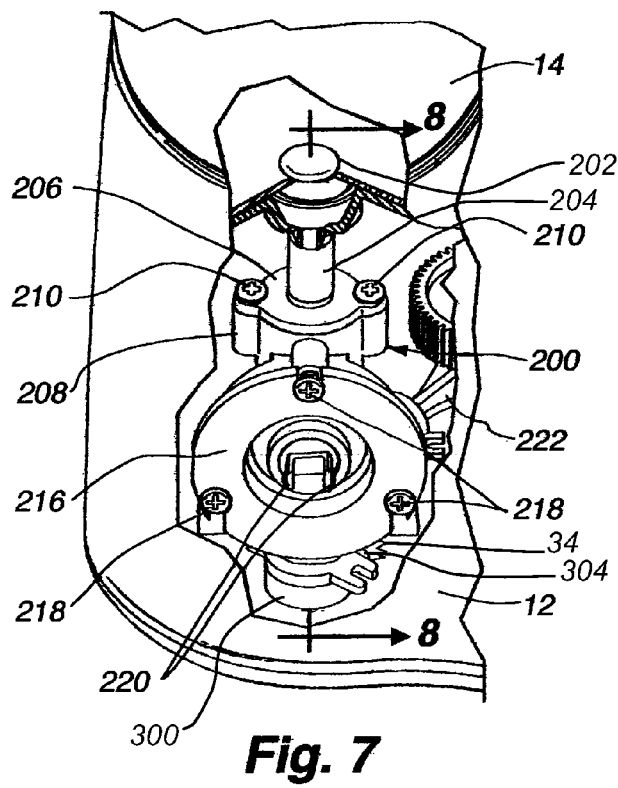
FIG. 7 depicts a perspective view of the lower left portion of the embodiment depicted in FIG. 1 with the knob, the switch, and a portion of the base unit and the reservoir removed to show a segment of the pump and a related flow path between the reservoir and the pump.

FIG. 7 depicts a perspective view of the lower left portion of the embodiment depicted in FIG. 1 with the knob 40, the switch 38, a portion of the base unit 12 and a portion of the reservoir 14 removed to show a segment of the pump 200 and a related fluid flow path between the reservoir 14 and the pump 200. FIG. 7 also depicts a mechanism (described below) for adjusting the fluid pressure delivered to the tip 24 by the pump 200. As shown in FIG. 7, a reservoir valve 202 may be connected to a tube stand 204, as described in more detail below. The tube stand 204 may be connected to a pump inlet body 206, which may be connected to a pump body 208 with fasteners 210 (such as screws). A flow control 216 may also be connected to the pump body 208 with fasteners 218 such as screws. The flow control 216 may include a pair of prongs 220 for attaching the knob 40 to the flow control 216. A piston 222 (received within a piston housing) may be operatively associated with the pump body 208 as described in more detail below. The pump body 208 may also be connected to a fitting 304, which may be used to fluidly communicate the tube 34 with the pump 200.

Figure 8A:
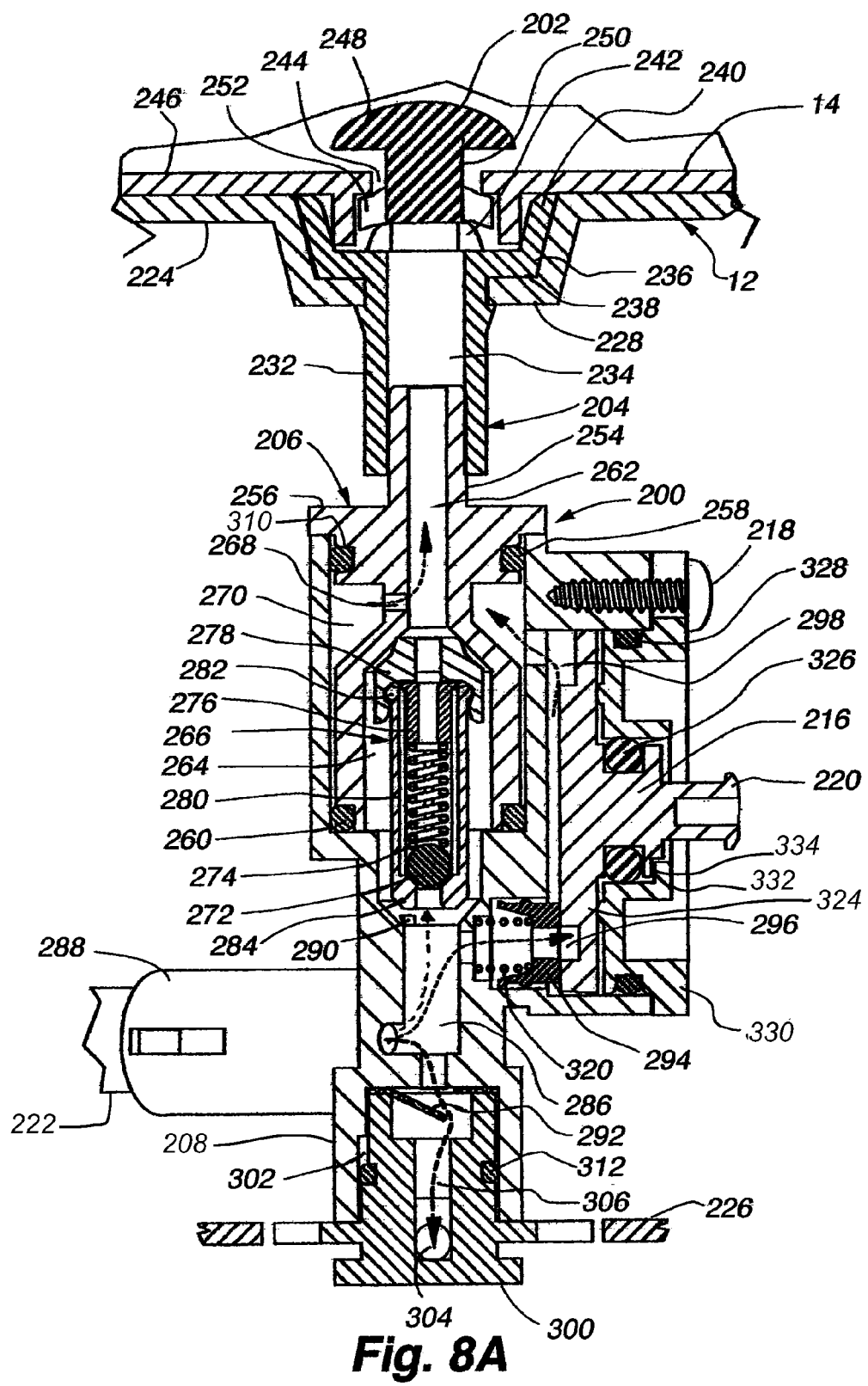
FIG. 8A depicts a first cross-sectional view of the pump body and various components depicted in FIG. 7, viewed along line 8-8 in FIG. 7, and showing the flow paths of a fluid during the forward stroke of a piston.

FIG. 8A depicts a cross-sectional view of a portion of the pump 200, the base unit 12, and the reservoir 14 viewed along line 8-8 of FIG. 7. The base unit 12 may include an upper base unit segment 224 and a lower base unit segment 226. The upper base unit segment 224 may include a seat 228 extending from the upper base unit segment 224 into a cavity defined by the mating of the upper and lower base unit segments 224, 226. The seat 228 may receive the tube stand 204, which typically includes a tube stand shaft 232 defining a tube stand fluid passage 234. The tube stand 204 may further include a tube stand collar 236 comprised of a tube stand base 238 and defining a tube stand opening in fluid communication with the tube stand fluid passage 234. A tube stand sidewall 240 extends from the tube stand base 238. Together, the tube stand base and sidewall 238, 240 may fit snugly within the seat 228.

One or more tube stand projections 242 may extend from the tube stand base 238 to contact the reservoir valve 202, which seats within a reservoir opening 244 defined in a reservoir base 246. The tube stand projections 242 lift a reservoir valve head 248 off the reservoir base 246, thereby enabling fluid to enter and exit the reservoir 14 through the reservoir valve 202 and tube stand fluid passage 234. In particular, when the reservoir 14 is supported by the base unit 12, the tube stand 204 and the reservoir valve 202 are generally co-axially aligned and the tube stand projections 242 engage a reservoir valve shaft 250. This pushes the reservoir valve head 248 away from the reservoir base 246. As the reservoir valve head 248 is pushed away, reservoir valve legs 252 extending from the reservoir valve shaft 250 bear against the reservoir base 246. The reservoir valve legs 252 may be sufficiently flexible to deform under pressure, thereby allowing the reservoir valve head 248 to be lifted, but also dimensioned to prevent the reservoir valve 202 from being entirely pushed out of the reservoir opening 244 in the reservoir base 246 by the tube stand projections 242. When the reservoir 14 is removed from the base unit 12, the deformed reservoir valve legs 252 will return to their original state, thereby returning the reservoir valve head 248 to its original position of bearing against the reservoir base 246. Gravity and/or fluid pressure may also aid in returning the reservoir valve head 248 to its original position.

The tube stand 204 may be connected to a portion of the pump inlet body shaft 254, which may be received within the tube stand fluid passage 234. The pump inlet body shaft 254 may include a first portion received within the tube stand fluid passage 234 and a second portion received within a first aperture of the pump body. The first and second portions of the pump inlet body shaft 254 are connected by a necking region. Proximate the necking region, a pump body inlet flange 256 may be formed as a portion of the pump inlet body 206 and may bear against an end surface of the pump body 208. An inlet groove formed on an upper portion of the pump inlet body 206 may receive a first base O-ring 258. Near the free end of the second portion of the pump inlet body shaft 254, the shaft 254 may form an inward step in profile. When the pump inlet body 206 is received within the pump body 208, this inward step and the pump body's inner surface may define a space for receiving a second base O-ring 260. The functions of the first and second base O-rings 258, 260 are described below.

The first portion of the pump inlet body shaft 254 may define a pump inlet fluid passage 262 in fluid communication with an interior pump chamber 264 defined by the necking region portion and second portion of the pump inlet body shaft 254. The pump inlet fluid passage 262 may increase in cross-sectional area after the necking region to define the interior pump chamber 264 in which a check valve assembly 266 is located. The pump inlet body shaft 254 may include a return hole 268 located within the necking region, which may enable fluid communication between the pump inlet fluid passage 262 and a return chamber 270 defined by the combination of pump inlet body's outer surface and the pump body's inner surface.

The check valve assembly 266 may contain a ball 272, a check valve spring 274, a seat relief 276, and a valve cap 278. The check valve assembly 266 may include a check valve shaft 280, in which the ball 272, check valve spring 274, and seat relief 276 may be positioned. Generally, the ball 272 seats at one end of the check valve shaft 280 (i.e., the end furthest from the pump inlet). At the other end, the check valve shaft 280 may include a check valve lip 282 to mate with a valve cap groove defined by the valve cap body, thereby creating a snap-fit connection between the valve cap 278 and the check valve shaft 280.

A bottom surface of the valve 278 cap may abut the seat relief 276. Further, an internal passage runs through the valve cap interior, providing a fluid connection between the pump inlet fluid passage 262 and the interior of the check valve assembly 266. In a likewise manner, fluid flowing through the internal passage of the valve cap 278 may enter the seat relief interior, which is generally hollow. In this manner, fluid may be conveyed from the reservoir 14, through the space between the reservoir valve head 248 and reservoir base 246, into the tube stand fluid passage 234, into the pump body 208 through the pump inlet fluid passage 262, through the valve cap 278 and into check valve shaft 280.

However, because the ball 272 of the check valve assembly 266 seats against the check valve base 284 and is biased by the check valve spring 274, the opposing end of the check valve assembly 266 is blocked by the ball 272. Thus, fluid cannot exit the check valve assembly 266 during normal operation of the embodiment. Rather, fluid may flow about the exterior check valve assembly 266. Typically, this fluid flows through the interior pump chamber 264 and ultimately flows out a pump body outlet 286.

Fluid flows from the reservoir 14 to the pump body outlet 286 only on a backstroke of the piston 222 connected to the pump body outlet 286 through a piston housing 288 (as described below). Suction generated by the piston 222 backstroke pulls the check valve assembly 266 down within the interior pump chamber 264. Downward motion of the check valve assembly 266 is arrested by a check valve stop 290 projecting into the interior pump chamber 264. The check valve stop 290 prevents the bottom of the check valve assembly 266 from contacting the bottom of the interior pump chamber 264. Were the check valve assembly bottom and interior pump chamber bottom to impact, there would be no path for fluid flow from the interior pump chamber 264 to the pump body outlet 286. By maintaining a distance between the respective bottoms, fluid may flow between the interior pump chamber 264 and pump body outlet 286. Further, during the piston 222 backstroke, the aforementioned suction generally draws fluid from the interior pump chamber 264 into the pump body outlet 286.

On a forward stroke of the piston 222, positive pressure is generated in the pump body outlet 286 (and, by extension, in portions of the present embodiment fluidly connected to the pump body outlet 286). This positive pressure has several effects. First, it forces fluid out of the pump body outlet 286. Fluid may flow through a reed valve 292 (described below), into a bypass valve 294, or push against the check valve base 284. In many cases, fluid flows through two or all three fluid paths simultaneously. FIG. 8A depicts the fluid flow paths available during a forward stroke of the piston 222.

During the forward stroke, fluid presses against the check valve base 284, lifting the check valve assembly 266 off the check valve stop 290. Typically, the pressure of the forward stroke is sufficient not only to unseat the check valve assembly 266 from the check valve stop 290, but to drive the exterior (top) of the valve cap 278 against the interior surface of the interior pump chamber 264. The abutment of valve cap 278 and interior pump chamber surface forms a substantially fluid-tight seal. Thus, although fluid may enter the interior pump chamber 264 from the pump body outlet 286 during the piston's forward stroke, the fluid may not enter the pump inlet fluid passage 262 or flow any further towards the reservoir 14.

Fluid may also flow through the bypass valve 294 during the piston's forward stroke. Generally, fluid flowing through the bypass valve 294 enters a flow regulation conduit 296 formed on the back of the flow control 216. The back of the flow control 216 abuts the bypass valve 294. Fluid exiting the bypass valve 294 from the pump body outlet 286 enters the flow regulation conduit 296.

It should be noted that the body of the bypass valve 294 extends slightly outwardly from the exterior wall of the pump body 208. The exterior of the pump body 208 and back of the flow control 216 cooperate to form a return channel 298 (see FIG. 8A) fluidly connected to the flow regulation conduit 296. This return channel 298 is further fluidly connected to the return chamber 270 formed by the interior surface of the pump body 208 and the pump inlet body 206. As depicted in FIG. 8A, the return chamber 270 is outside the interior pump chamber 264 and in fluid communication with the pump inlet fluid passage 262.

Fluid flowing through the bypass valve 294 and into the flow regulation conduit 296 impacts the back of the flow control 216. The fluid, forced by the pressure of the piston's forward stroke, is diverted into flow regulation conduit 296 and thence to the return channel 298, from which it may enter the return chamber 270. This effectively permits fluid flowing through the return channel 270 to bypass the check valve assembly 266 and interior pump chamber 264. From the return chamber 270, fluid may flow up the pump inlet fluid passage 262 and into the tube stand fluid passage 234. If the return fluid is under sufficient pressure to overcome the fluid pressure of fluid flowing from the reservoir 14 into the tube stand fluid passage 234 under the influence of gravity, the fluid may flow back into the reservoir 14 through the open reservoir valve 202.

It should be noted that the bypass valve 294 permits fluid flow in two directions, namely from the pump body outlet 286 to the return channel 298 and from the return channel 298 to the pump body outlet 286. (That is, the bypass valve 294 is a two-way valve.) Accordingly, fluid may flow from the pump inlet fluid passage 262, into the return chamber 270, down the return channel 298 and into the pump body outlet 286 during the piston's backward stroke.

Figure 11A:
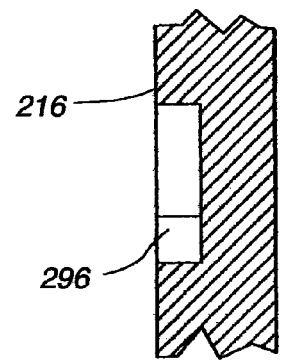
FIG. 11A depicts a cross-section view of a portion of the flow control, taken along line 11A-11A in FIG. 9.
Figure 11B:
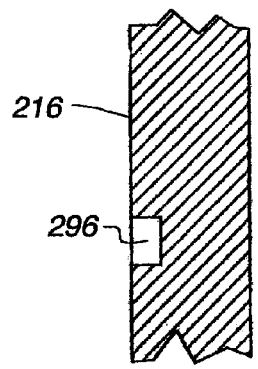
FIG. 11B depicts a cross-section view of a portion of the flow control, taken along line 11B-11B in FIG. 9.
Figure 11C:
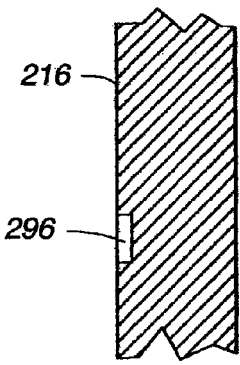
FIG. 11C depicts a cross-section view of a portion of the flow control, taken along line 11C-11C in FIG. 9.

The flow control 216 may adjust the volume of fluid that may flow through the bypass valve 294 and into the return channel 298. As the flow control 216 is rotated, the dimensions of the flow regulation conduit 296 vary. Essentially, the cross-section of the flow regulation conduit 296 adjacent the bypass valve 294 increases or decreases, depending on the direction in which the flow control 216 is turned. For example, in one embodiment rotating the flow control 216 clockwise (as viewed from the front of the flow control) may decrease the cross-sectional area of the flow regulation conduit 296 adjacent the bypass valve 294, while rotating the flow control counterclockwise may increase the cross-sectional area of the conduit 296. FIGS. 11A-11C depict cross sectional views of a portion of the flow control 216 depicting the size of the flow regulation conduit 296 at different points along the conduit's length. FIGS. 11A-11C are cross-sectional views viewed along their respective lines shown in FIG. 9.

Figure 8B:
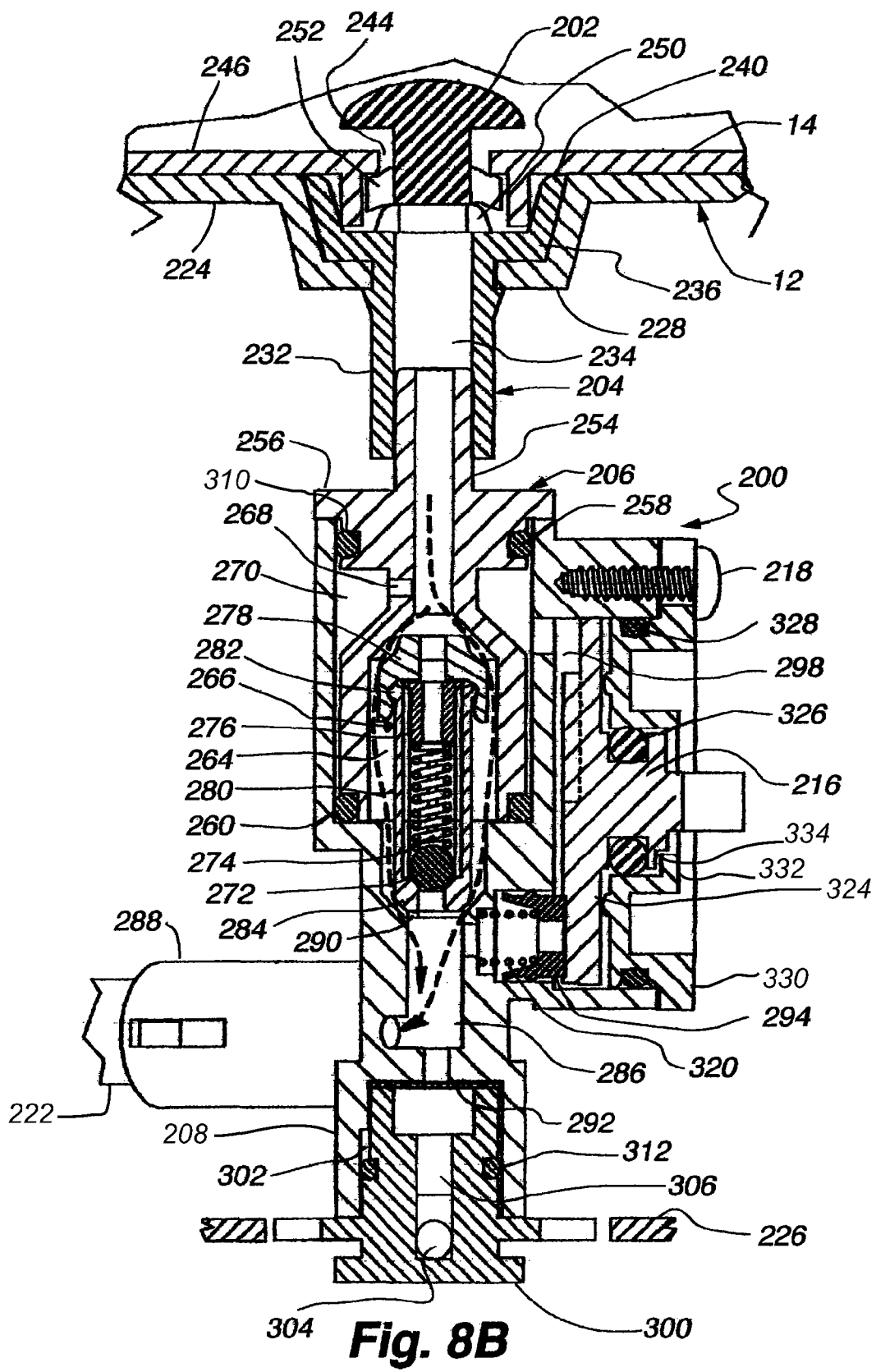
FIG. 8B depicts a second cross-sectional view of a portion of the pump, the base unit and the reservoir viewed along line 8-8 in FIG. 7, and showing the flow paths of a fluid during a backstroke of the piston.

As the dimensions of the flow regulation conduit 296 adjacent the bypass valve 294 increase, more fluid may be accepted from the bypass valve 294 and diverted to the return channel 298. Conversely, as the dimensions of the flow regulation conduit 296 adjacent the bypass valve 294 decrease, the volume of fluid that may exit the bypass valve 294 into the conduit 296 (and return channel 298) likewise decreases. In this manner, a user may adjust the flow volume through the return channel 298 and into the return chamber 270 as desired. As shown in FIG. 8B, the fluid regulation conduit 296 may be adjusted to prevent fluid from exiting the bypass valve 294 into the return channel 298.

The third fluid exit from the pump body outlet 286 is via the reed valve 292 fluidly connected to a fitting 300. The fitting 300 seats within a pump body base opening 302 formed in the bottom of the pump body 208, as shown in cross-section on FIGS. 8A-8C. One end of the aforementioned tube 34 is connected to a fitting outflow 304, and a fitting fluid path 306 extends from a top of the fitting 300, adjacent the reed valve 292, to the fitting outflow 304. Accordingly, fluid entering the fitting 300 may flow through the fitting outflow 304, into the tube 34, through the handle 26, and ultimately into the tip 24 in order to irrigate or spray fluid into a user's mouth.

The reed valve 292 generally permits fluid flow only when open. As the piston executes a forward stroke, fluid pressure forces the reed valve 292 into an open position. That is, the reed of the reed valve 292 is pushed downward into the fitting fluid path 306. Thus, fluid may be driven by the piston 222 through the reed valve 292, into the fitting fluid path 306, through the associated fitting outflow 304 and into the tube 34. Ultimately, and by means of the tube 34, the piston 222 propels fluid into the tip 24, as well as out of the tip distal end 186.

It has been previously explained how adjusting the flow control 216 can vary fluid flow out of the pump body outlet 286 and through the return channel 298. It should be appreciated that as more fluid passes to the return channel 298, less fluid is available to enter the fitting fluid path 306 (and tube 34) through the reed valve 292. Accordingly, increasing the flow through the return channel 298 diminishes fluid flow to the tip 24, which decreases the fluid pressure of fluid exiting the tip 24. In this manner, the user may directly control the volume of fluid exiting the reservoir 14 and being pushed by the piston 222 through the tip 24. Thus, the user may control fluid flow out of the tip 24 by manipulating the flow control 216, which enables the user to control the fluid pressure of fluid exiting the tip 24.

In summary, the flow path for fluid during a backstroke of the piston 222 follows. Fluid may exit the reservoir 14 through the reservoir opening 244 in which the reservoir valve 202 resides, flowing into the tube stand fluid passage 234. The fluid may enter the pump inlet fluid passage 262 from the tube stand fluid passage 234, flow into the interior pump chamber 264 and around the check valve assembly 266, and into the pump body outlet 286. The backstroke suction draws the check valve assembly 266 down within the interior pump chamber 264 to permit fluid flow between the pump inlet fluid passage 262 and interior pump chamber 264.

During a forward stroke of the piston, fluid may be propelled from the pump body outlet 286, through the reed valve 292, into the fitting fluid path 306, through the fitting outlet 304, into the tube 34, through the various fluid passages 72, 78, 82, 84 of the handle 26, into the tip 24, and out of the tip distal end 186. Additionally, the forward pressure of the piston 222 may drive the check valve assembly 266 upward within the interior pump chamber 264, seating the valve cap 278 against an interior surface of the pump inlet body 206. This chokes off fluid flow between the interior pump chamber 264 and the pump inlet fluid passage 262. Also during the forward stroke of the piston 222, some fluid may be diverted through the bypass valve 294, into the flow regulation conduit 296, along the return channel 298 and into the return chamber 270. This fluid may then enter the pump inlet fluid passage 262, the tube stand fluid passage 234, and ultimately flow, if under sufficient pressure, into the reservoir 14 through the reservoir valve opening.

Additionally, the present embodiment includes a pause mode. During the pause mode, no fluid flows into or out of the tip 24. This may be useful, for example, when a user wishes to pause oral irrigation. To initiate a pause mode, a user or operator may depress the button 30 on the handle 26. Depressing the button 30 forces the stop plunger 86 into the fourth fluid passage 84. Because the stop plunger 86 is aligned within the fourth fluid passage 84 and transverse to the direction of fluid flowing into the valve body 56 from the tube 34, motion of the stop plunger 86 is not opposed by the pressure of fluid flowing through the valve body 56 when the button 30 is pressed or released. The base of the stop plunger 86 may abut a sidewall of the fourth fluid passage 84. The stop plunger 86, possibly in conjunction with at least one plunger O-ring 156 disposed about it, may prevent fluid flow into the fourth fluid passage 84 from the tube 34. Since fluid cannot enter the fourth fluid passage 84, any fluid pressure and flow is prevented from reaching the tip 24. Accordingly, fluid cannot exit the tube 34. Further, since the stop plunger 86 is aligned transversely to fluid flowing into the valve body 56 from the tube 34, little or no fluid pressure opposes the closing of the fourth fluid passage 84 by the stop plunger 86. The third spring 158 is biased to return the stop plunger 86 to its original position when a user stops depressing the button 30. It should be noted that the third spring 158 does not have to exert force against any fluid pressure to return the stop plunger 86 to its initial position, due to the alignment of the plunger 86.

Depressing the stop plunger 86 additionally forces fluid to seek a different exit from the pump body outlet 286, insofar as more fluid cannot flow through the reed valve 292, into the fitting 300 and thence to the tube 34. (Some fluid may so flow after depressing the button 30, but only enough to fill the fitting 300, fitting outflow 304, and tube 34. Once these elements are filled with fluid, additional fluid may not flow along this route.) Further, the fluid flow volume through the return channel 298 is limited by the size of the flow regulation conduit 296.

Figure 8C:
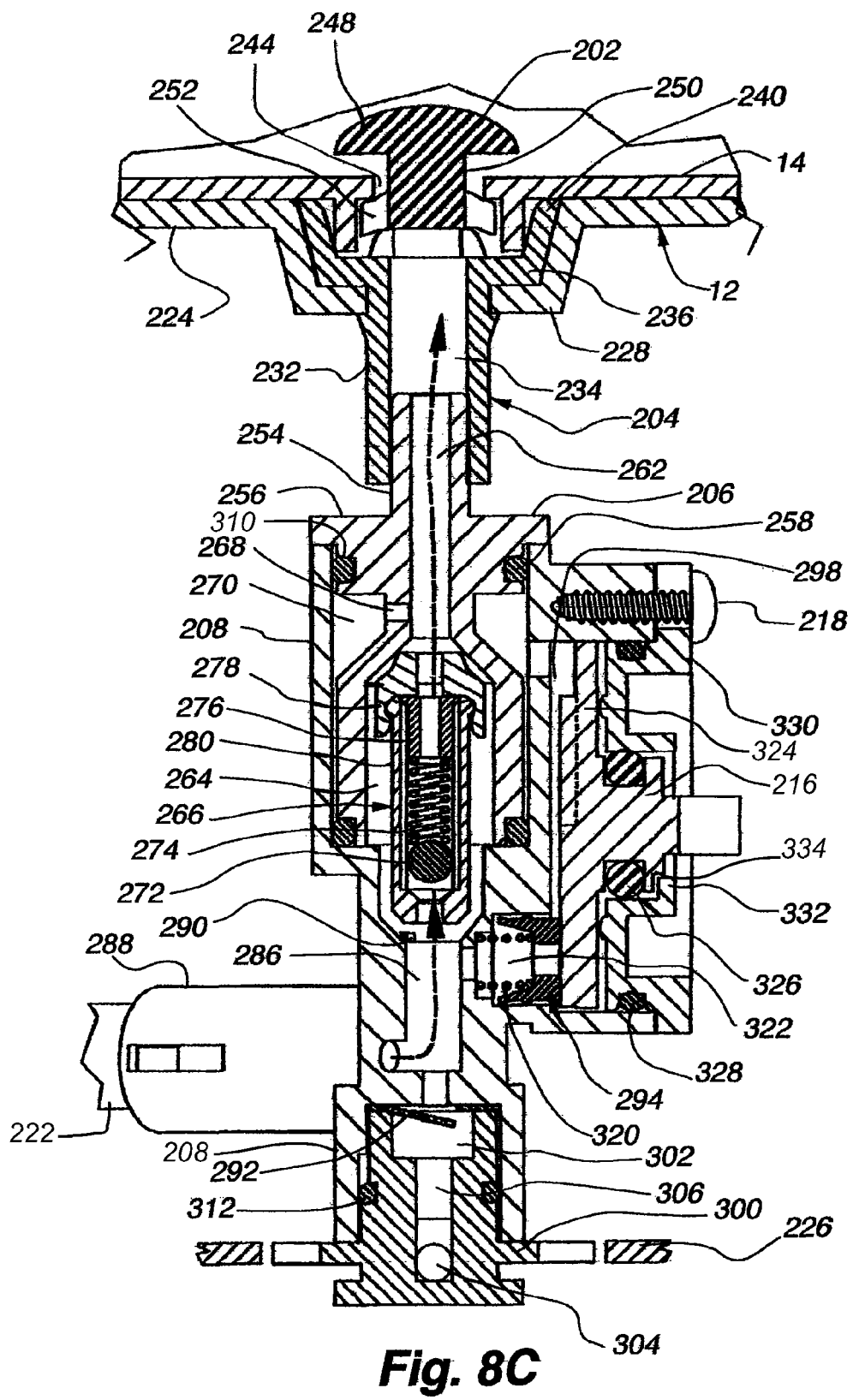
FIG. 8C depicts a third cross-sectional view of a portion of the pump, the base unit and the reservoir viewed along line 8-8 in FIG. 7, and showing fluid flow during a pause operation of the embodiment.

As fluid pressure builds under such a situation and the piston 222 performs a forward stroke, the fluid may flow up into the interior pump chamber 264 and push against the check valve base 284. As previously mentioned, this unseats the check valve assembly 266 from the check valve stop 290. However, if sufficient fluid pressure exists, the fluid may press against the ball 272 in the check valve shaft 280 and drive it against the check valve spring 274. As shown in FIG. 8C, when the fluid pressure exceeds the tension of the check valve spring 274, the ball 272 may unseat from the check valve base 284 and move upward within the check valve shaft 280. When the ball 272 moves sufficiently upward, fluid may flow from the interior pump chamber 264, through the check valve assembly 266, and into the pump inlet fluid passage 262. Ultimately, such fluid may return to the reservoir 14.

By providing this alternative flow path during the pause mode, damage to the piston 222 may be avoided.

Figure 9:
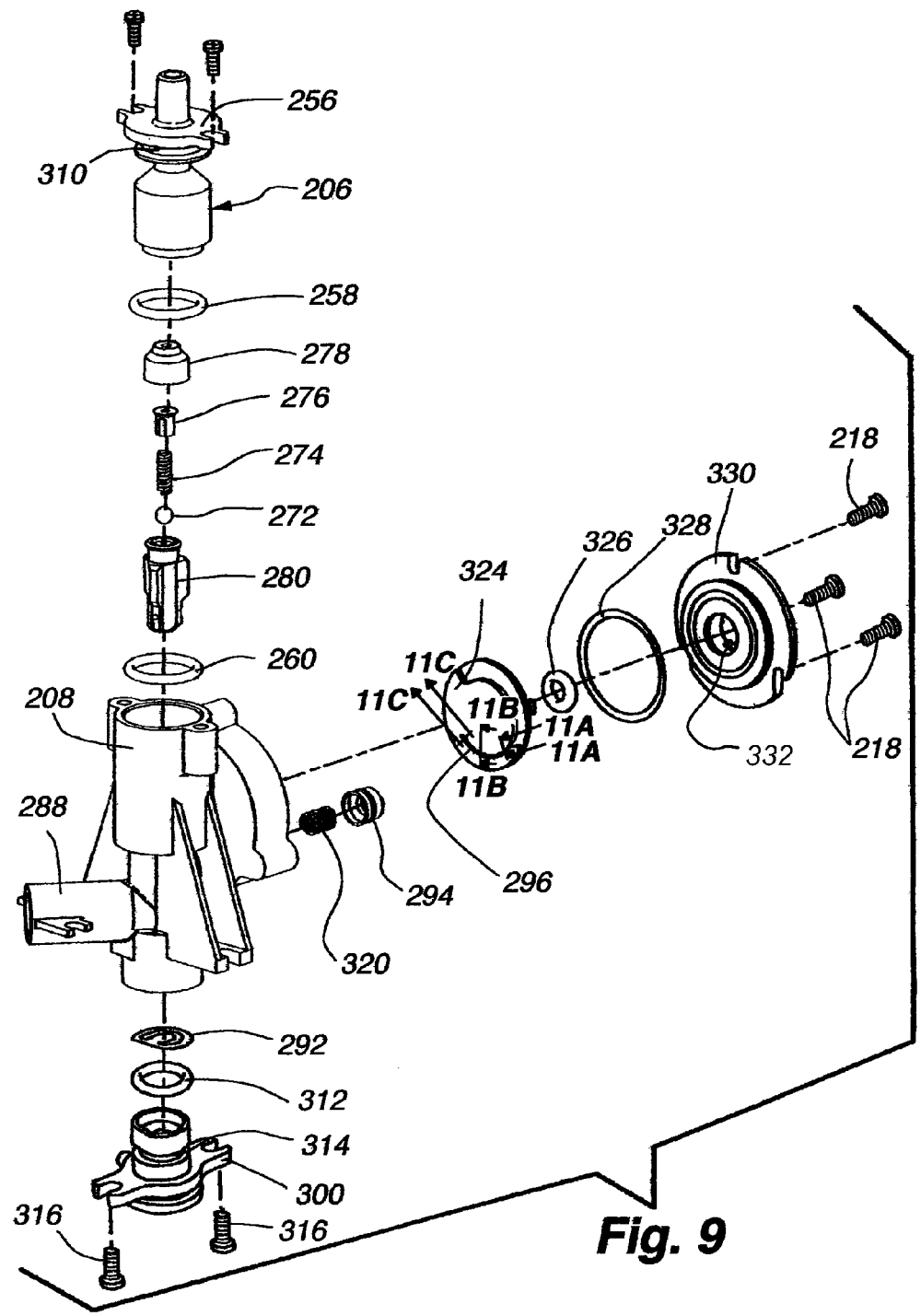
FIG. 9 depicts an exploded perspective view of the pump body and flow control depicted in FIG. 8.
Figure 10:
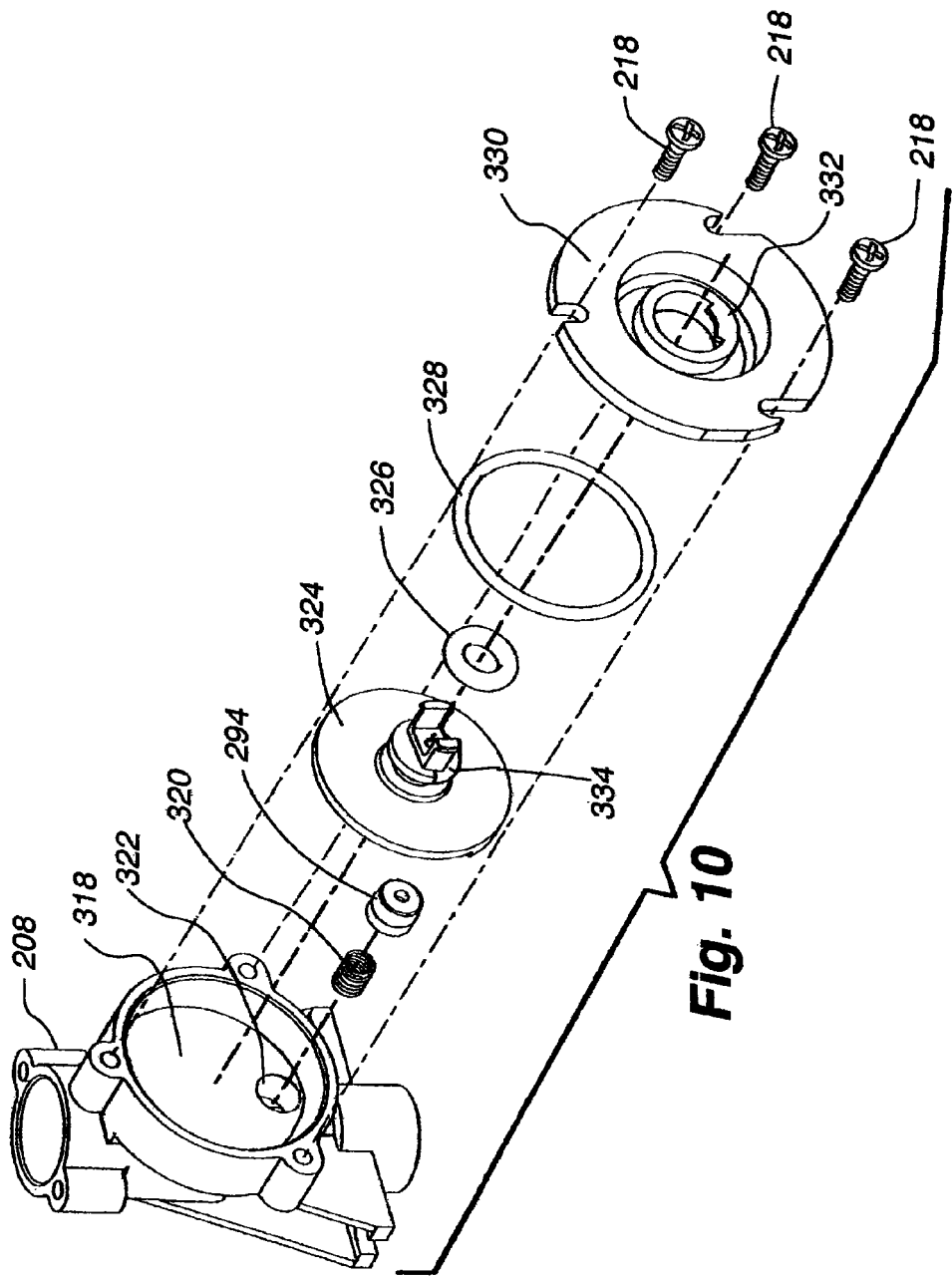
FIG. 10 depicts an exploded perspective view of the flow control depicted in FIG. 9.

FIG. 9 is an exploded perspective view of an unassembled state of the various components depicted in FIG. 8. Similarly, FIG. 10 depicts an exploded perspective view of the pump body 208 and the flow control 216. With reference to FIGS. 8, 9 and 10, assembly of the pump body 208, fitting 300, check valve assembly 266, flow control 216, bypass valve 294, and certain other elements will now be described.

The ball 272, check valve spring 274 and seat relief 276 may be placed within the check valve shaft 280 and the valve cap 278 affixed to the check valve shaft 280 to form the check valve assembly 266. The second base O-ring 260 and the check valve assembly 266 may be placed in the hollow pump body 208. Generally, the second base O-ring 260 abuts the interior pump body wall.

The first base O-ring 258 may fit within an inlet groove 310 formed on an upper, outer portion of the pump inlet body 206. The pump inlet body 206 may then be mated to the pump body 208, such that a pump inlet body flange 256 rests atop the pump body 208. The majority (although not all) of the pump inlet body 206 may be received within the hollow interior of the pump body 208. An inside wall of the pump inlet body 206 forms a sidewall of the interior pump chamber 264, while a stepped interior base of the hollow pump body 208 forms a base of the interior pump chamber 264. Similarly, the base of the pump inlet body groove 310 forms a top of the return chamber 270 and the interior wall of the hollow pump body 208 forms a sidewall of the return chamber 270.

The second base O-ring 260 generally prevents fluid from flowing out of the return chamber 270, along the exterior of the pump inlet body 206 and into the pump body outlet 286. In a like manner, the first base O-ring 258 reduces or stops fluid leakage out of the return chamber 270, along the pump body inlet groove 310 and into the atmosphere.

The pump inlet body 206 may be fastened or affixed to the pump body 208 by adhesive, fasteners (e.g. screws, bolts or the like), sonic welding, and so forth. In the embodiment shown in FIG. 9, one screw 210 passes through each of two U-shaped protuberances formed on opposing ends of the pump inlet body flange 256. The screws 210 are received in screw holes formed on the pump body 208.

A fitting O-ring 312 may be placed in a fitting groove 314 formed on the fitting exterior. The reed valve 292 may be placed atop the fitting 300, and the fitting 300, reed valve 292, and fitting O-ring 312 all inserted into the pump body base opening 302. When so situated, the fitting O-ring 312 contacts the interior wall of the pump body base opening 302, and reduces or prevents fluid from leaking out of the pump body outlet 286 and along the fitting exterior (see FIG. 8A). Fasteners 316, such as screws, an adhesive, and so forth, may hold the fitting 300 to the pump body 208 and within the aforementioned opening 302. In particular, the fasteners 316 may connect the fitting 300 not only to the pump body 208 but also to the piston housing 288. The piston housing 288 may be formed with the pump body 208 or may be formed separately and affixed thereto.

The assembly of the flow control 216 and bypass valve 294, as well as their fitting to the pump body 208, will now be discussed with particular respect to FIGS. 9 and 10.

The flow control receptacle 318, formed on the pump body 208, is generally cylindrical with a flat, circular end wall. This end wall of the flow control receptacle 318 and the back of the flow control 216 combine to define the aforementioned return channel 298. It should be noted the flow control receptacle 318 may be formed integrally with the pump body 208 or may be formed separately and attached thereto.

A bypass spring 320 may be placed within a portion of the bypass valve 294. The bypass valve 294 and bypass spring 320 may be fitted in a bypass cavity 322 formed in the end wall of the flow control receptacle 318. The bypass cavity 322 is in fluid communication with the pump body outlet 286, such that fluid may flow into the bypass valve 294 from the pump body outlet 286 when the bypass valve 294 is seated in the bypass cavity 322.

The flow control 216 may consist of multiple parts. For example and as illustrated in FIG. 10, the flow control 216 may include a flow control backplate 324, a first flow control O-ring 326, a second flow control O-ring 328, and a flow control frontplate 330. The first flow control O-ring 326 may be placed about an exterior groove formed below a neck of the flow control backplate 324. The flow control backplate 324 may be mated or placed adjacent to the flow control frontplate 330. Generally, the neck of the flow control backplate 324 passes through a central hole in the flow control frontplate 330 and projects outward. Further, the flow control backplate and frontplate 324, 330 sandwich the second flow control O-ring 328 therebetween, as shown to best effect in the cross-sectional view of FIG. 8A.

The flow control frontplate 330 may be affixed to the flow control receptacle 318, for example by an adhesive, fastener (s), sonic welding, and so forth. Once the flow control frontplate 330 is affixed to the flow control receptacle 318, it generally will not turn or rotate. However, the flow control backplate 324 may freely rotate or turn about at least a portion of its axis, insofar as it is fixedly connected to neither the flow control receptacle 318 nor the flow control frontplate 330.

A control stop 332 may project inwardly from the central hole of the flow control frontplate 330 and rest in a backplate groove 334 formed on or near the neck of the flow control backplate 324 (see FIG. 10). The flow control backplate 324 may rotate until an edge of the backplate groove 334 impacts the control stop 332, which in turn prevents the flow control backplate 324 from rotating further. As the flow control backplate 324 rotates, the portion of the flow regulation conduit 296 adjacent the bypass valve 294 changes. This, as described above, may vary the fluid flow through the return channel 298.

Figure 12:
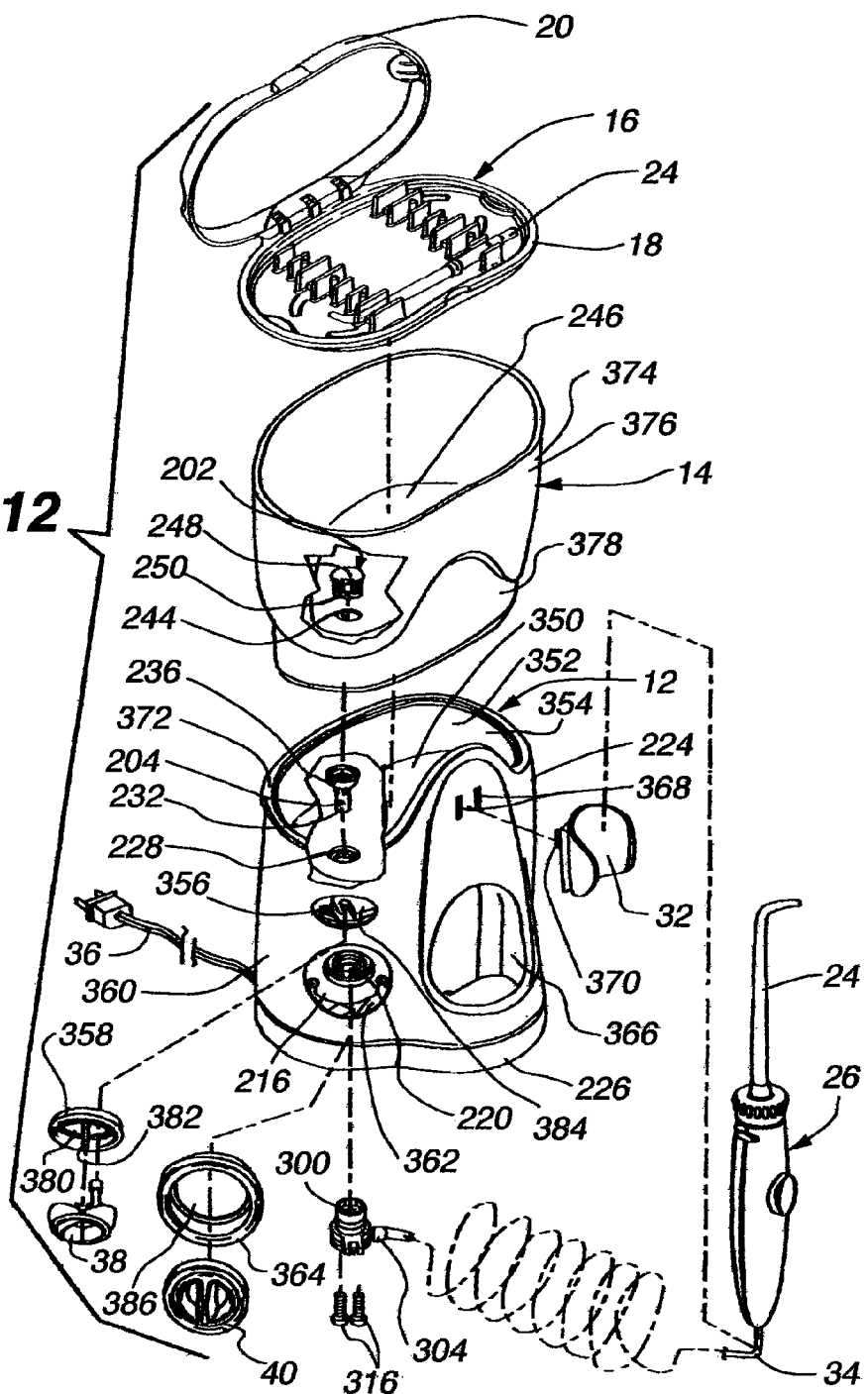
FIG. 12 depicts an exploded, front perspective view of various components of the embodiment depicted in FIG. 1

FIG. 12 depicts an exploded, front perspective view of various components of the embodiment depicted in FIG. 1 with portions of the base unit 12 and reservoir 14 removed to better show the reservoir opening 244 in the reservoir base 246 and the seat 228 in the base unit 12. The base unit 12 may include upper and lower base unit segments 224, 226. When joined, the upper and lower base unit segments 224, 226 may define a cavity for containing the pump 200. The upper base unit segment 224 may include a basin base 350 and a basin wall 352 extending from the basin base 350, which define a basin 354 for receiving a portion of the reservoir. As described in more detail below, the basin wall 352 may form a unique basin shape, which may facilitate alignment and receipt of the reservoir within the basin 354. The basin base 350 may include the seat 228 for receiving the tube stand 204.

A switch aperture 356 to receive the switch 38 and a switch molding 358 may be defined in a upper base unit wall 360 of the upper base unit segment 224, and a knob aperture 362 to receive the knob 40 and a knob molding 364 may also be defined in the upper base unit wall 360. Additionally, a tube aperture 366 to receive the tube 34 may be defined in the upper base unit wall 360, and clamp slots 368 that receive mating clamp tabs 370 to connect the clamp 32 to the upper base unit segment 224 may be also be defined in the upper base unit wall 360. A generally U-shaped power cord groove (not shown) for receiving the power cord 36 may also be defined in the upper base unit wall 360. A basin rim 372 may extend between and join the basin and upper base unit walls 354, 360, thereby providing a bearing surface for the reservoir 14.

The reservoir 14 may include the reservoir base 246 and a reservoir wall 374 extending from the base 246. The reservoir base and wall 246, 374 may define a volume for storing a fluid such as water. The reservoir wall 374 may be stepped, thereby defining an upper reservoir wall portion 376 and lower reservoir wall portion 378 connected by a surface for bearing on the basin rim 372 of the upper base unit segment 224. The lower reservoir wall portion 378 may be received within the basin 354 in the upper base unit segment 224. Further, the reservoir wall 374 may be outwardly curved along at least a portion of its back side and inwardly curved along at least a portion of its front side (or vice versa). These curved portions of the reservoir wall 374 typically mate with the basin wall 352 of the upper base unit segment 224. The different curved shapes of the front and back sides of the reservoir 14 and basin 354 generally ensure the reservoir 14 is aligned in a particular manner when received within the basin 354 of the upper base unit segment 224. This alignment may aid in placing the reservoir valve 202 above or adjacent to the tube stand 204. Although the reservoir 14 and basin 354 are described as having differently curved front and back surfaces, other shapes (e.g., such as trapezoidal, angled, scalene triangular, etc.) could be utilized. Any combination of shapes which uniquely permit the reservoir 14 and basin 354 to align in a single manner may be used.

The tube stand 204 may include a generally cylindrical tube stand shaft 232 with a generally partial-conical tube stand collar 236 formed on an end of the tube stand shaft 232. The reservoir valve 202 may include a generally cylindrical reservoir valve shaft 250 with a generally circular reservoir valve head 248 formed on an end of the reservoir valve shaft 250. The circular reservoir valve head 250 may encompass the reservoir opening 244 in the reservoir base 246, thereby substantially preventing a fluid from flowing through the reservoir opening 244 when the reservoir valve head 248 bears against the reservoir base 246. The reservoir valve 202 may also include four generally cubic shaped reservoir legs 252 extending from the reservoir valve shaft 250.

The switch molding 358 may include generally ovoid shaped body. The switch molding 358 may be attached to the base unit 12 using glue, epoxy, fasteners, sonic welding, or any other suitable known method of joining two items. The switch molding 358 may define a switch molding aperture 380 to receive the switch 38. The switch molding 358 may further include a switch molding column 382 extending across the switch molding aperture 380 to mate with a pair of notched, parallel walls extending from a V-shaped body of the switch 38. When the switch 38 is joined to the switch molding 358, the switch 38 may pivot around the switch molding column 382, thereby enabling the switch 38 to move a pump switch connector 384 that turns the pump 200 on and off as described in more detail below. The switch 38 may be joined to the pump switch connector 384 by receiving a circular switch arm, which is connected to the switch 38 via a switch shaft extending from the switch 38, within a switch connector slot defined by the switch connector's body.

The knob molding 364 may have a generally cylindrical body adapted to be received within the knob aperture 362 of the upper base unit segment 224. The knob molding 364 may be attached to the base unit 12 in a manner similar to the one described above for the switch molding 358. The knob molding 364 may define a knob molding aperture 386 to receive the knob 40. The knob 40 may have a generally cylindrical body adapted to permit the knob 40 to rotate within the knob molding aperture 386 when received therein. The knob 40 may further include a pair of recessed surfaces defining an elongated knob wall on one side, which may be gripped for rotating the knob 40. The knob 40 may be connected to the flow control 216 using the flow control prongs 220 extending from the flow control 216. Rotating the knob 40 within the knob molding aperture 386 will rotate the flow control 216, thereby permitting a user to selectively adjust the fluid pressure delivered by the pump 200 to the tip 24.

The fitting 300 may include the fitting outflow 304, which mates with the tube 34. The fitting 300 may be connected to the pump 200 or the base unit 12 using fasteners 316, thereby enabling the fitting 300 to be selectively detached from the pump 200. Because the fitting 300 may be selectively detached from the pump 200, the handle 26 may be readily decoupled from the pump 200, thereby enabling replacement of the handle 26, if desired.

Figure 13:
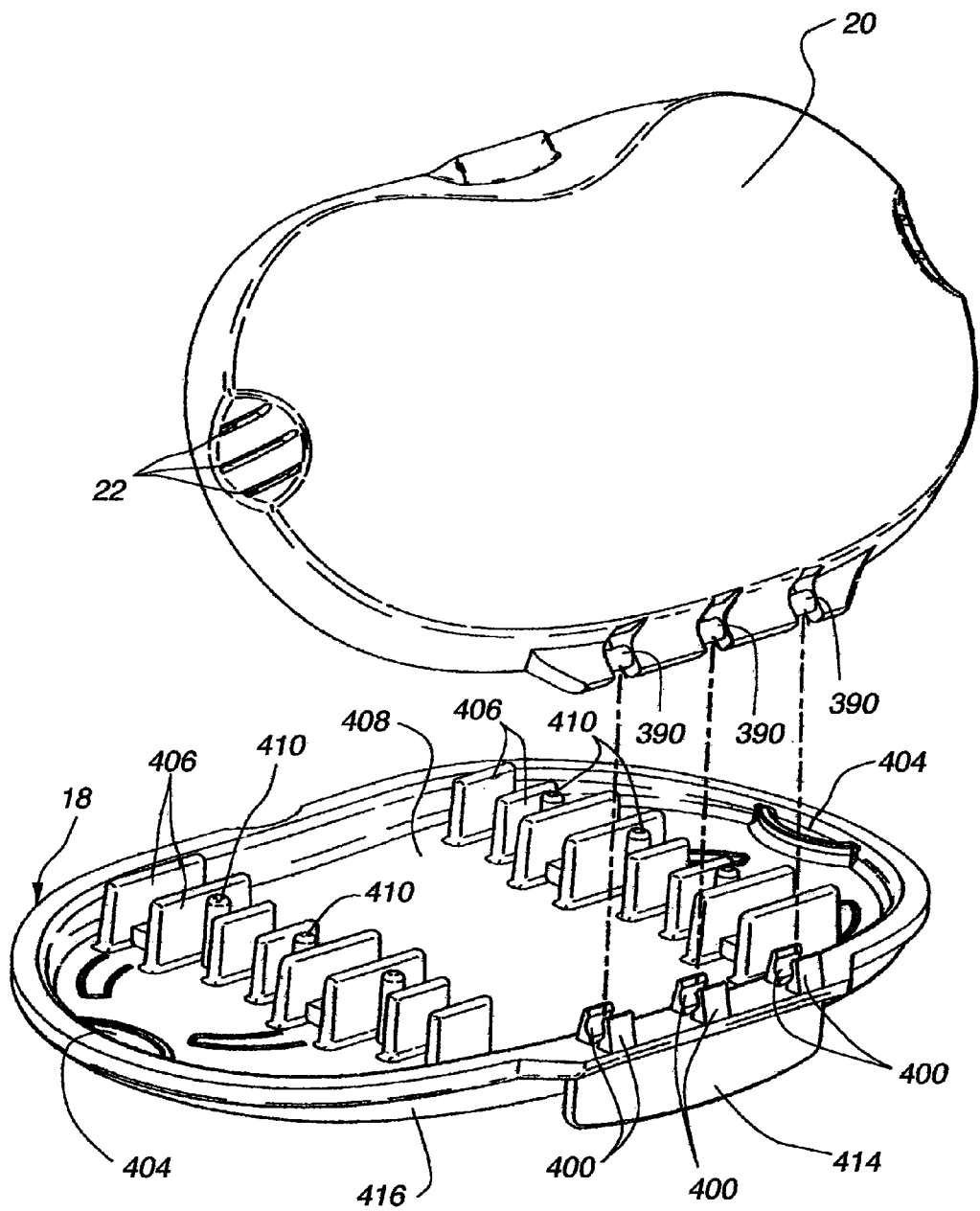
FIG. 13 depicts an exploded, perspective view of the container depicted in FIG. 1.

The container 16 may include the lid 20 and the container base 18. With reference to FIG. 13, the lid 20 and the container base 18 may be joined by receiving generally cylindrical lid shafts 390 between generally parallel container base walls 400 extending from container base 18 and configured to receive the lid shafts 390 therebetween, thereby forming a hinge that permits the lid 20 to be rotated relative to the container base 18 around a rotational axis defined by the longitudinal axis of the lid shafts 390. The container 16 may be opened and closed by rotating the lid 30 relative to the container base 18 around the rotational axis. When closed, inner surfaces of the lid 20 and the container base 18 define an enclosed volume capable of storing items such as tips 24. The lid 20 and the container base 18 may each have one or more ventilation holes 22, 404 within their respective bodies for ventilating the container 16 when it is closed, which may help dry any wet items placed within the contained and reduce moisture accumulation within the container 16, thereby reducing the potential growth of bacteria within the container 16.

One or more container tip walls 406 may extend from an upper container base surface 408 of the container base 18 and may be configured to accept a tip 24 (see FIG. 12) between adjacent container tip walls 406. One or more generally cylindrical container tip columns 410 may extend from the upper container base surface 408. The container tip columns 410 may have diameters approximately matching the diameter of the tip fluid passage, thereby supporting the tip 24 in a generally vertical orientation when receiving a container tip column 410 within the tip fluid passage. The container base 18 may have a stepped lower container base surface, thereby defining a container base bearing surface around the perimeter of the container base 18 for bearing on the reservoir 14 and a container base reservoir surface to be received within the reservoir opening. A container base rear wall 414 may extend from the container base bearing surface proximate the container hinge and generally parallel the container base lower wall 416 separating the container base bearing and container base reservoir surfaces. When the container 16 is supported on the reservoir, the container base rear wall 414 may be generally adjacent and parallel to the exterior surface of the reservoir wall 374, thereby aiding in the opening of the container 16 by bearing against this surface when the container 16 is opened by rotating the lid 20 relative to the container base 18.

Figure 14:
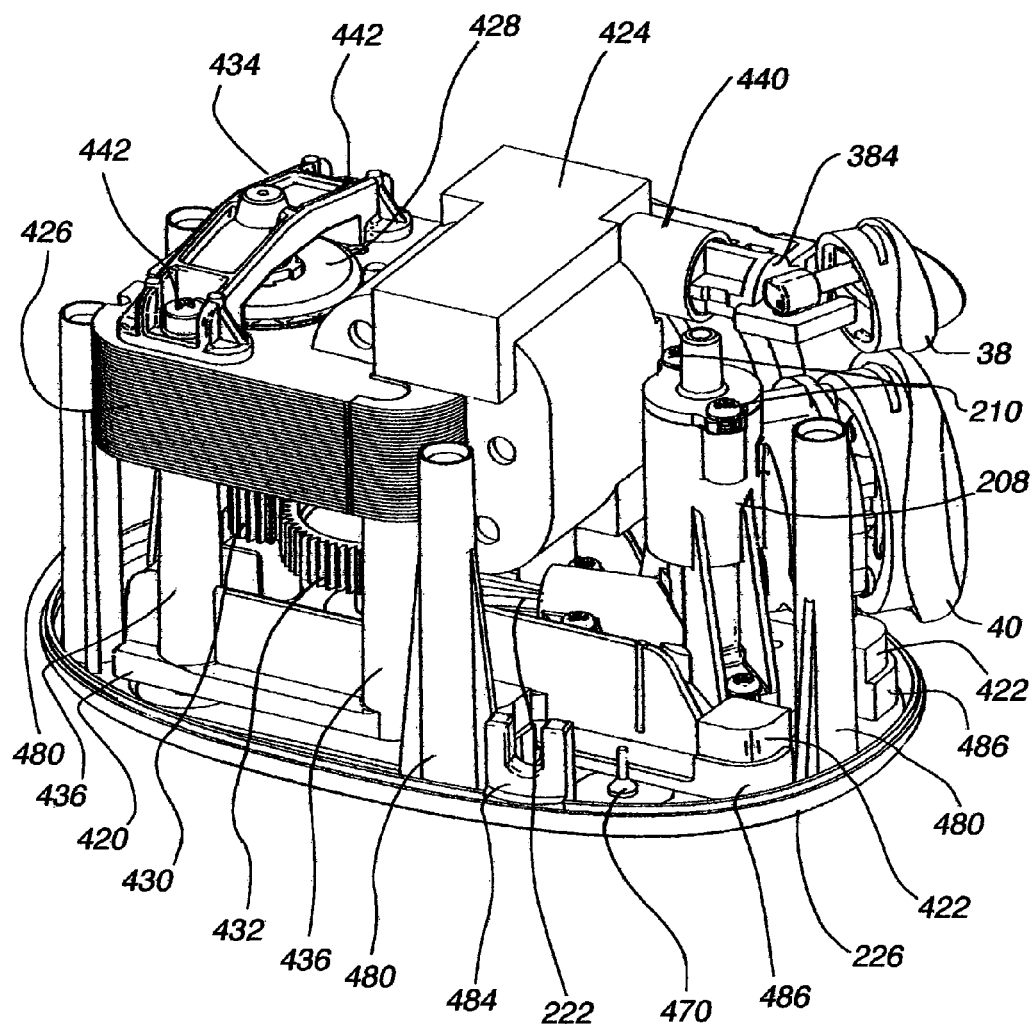
FIG. 14 depicts the embodiment shown in FIG. 1 with the upper base unit segment, the reservoir, the container, the handle, the tip, and the power cord not shown to better show the pump connected to the lower base unit segment.
Figure 18:
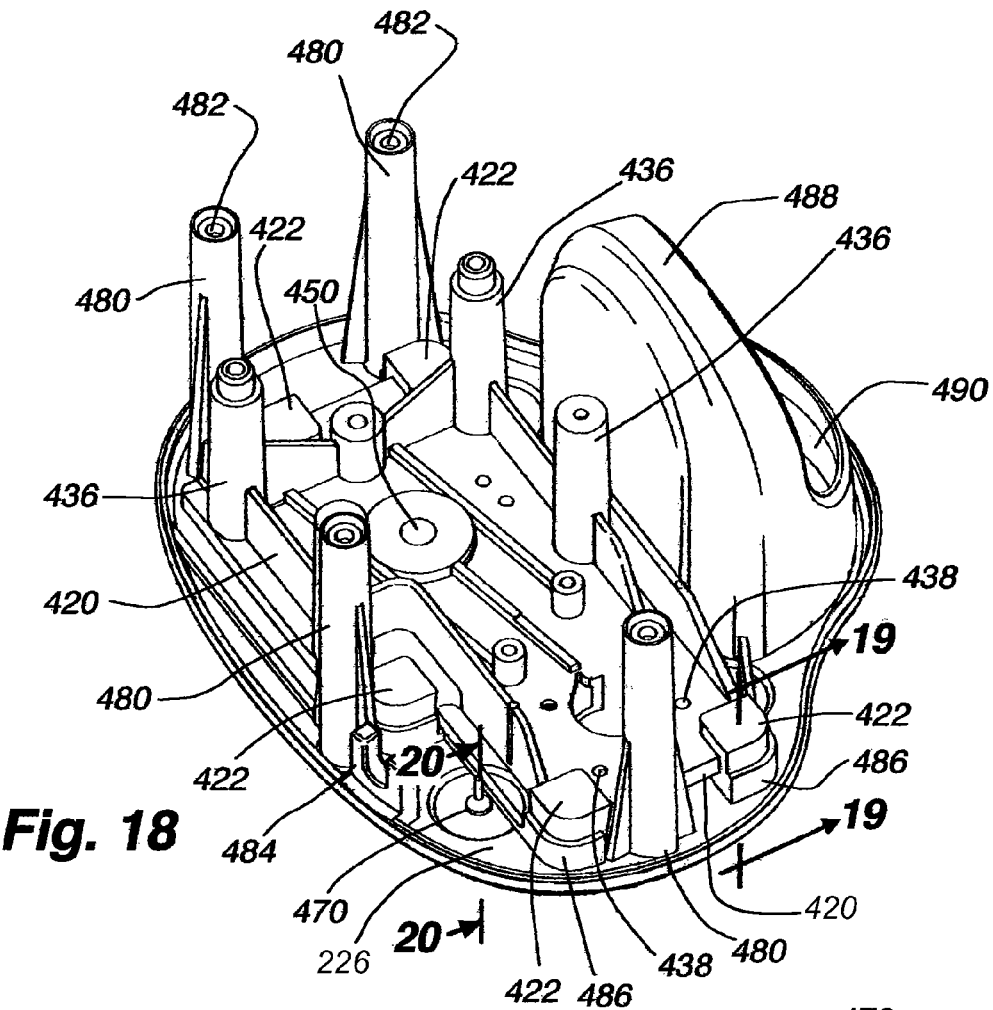
FIG. 18 is similar to FIG. 14 except all components of the pump, other than the pump chassis, have been removed to better show the pump chassis.

FIG. 14 is a perspective view of the embodiment depicted in FIG. 1 with the upper base unit segment 224, the reservoir 14, the container 16, the handle 26, and the power cord 36 not shown to better show the pump 200 connected to the lower base unit segment 226. FIG. 18 is similar to FIG. 14 except all components of the pump 200, other than the pump chassis 420, have been removed to better show the pump chassis 420. As described in more detail below, the pump 200 may be connected to the lower base unit segment 226 by pump mounts 422. The pump 200 may include the pump chassis 420, the pump body 208, a bobbin assembly 424, a stator assembly 426, a rotor 428, first and second gears 430, 432, the piston 222, a bracket 434, and the pump switch connector 384.

The pump chassis 420 may be used to support and align the various components of the pump 200. For example, the pump chassis 420 may include pump chassis posts 436 that support the stator assembly 426, and may include pump chassis holes 438 (see FIG. 18) for receiving fasteners that connect the pump body 208 to the pump chassis 420. The stator assembly 426, in turn, may support the bobbin assembly 424, which may include a switch housing 440 for receiving the pump switch connector 384 operatively associated with the switch 38. The stator assembly 426 may receive the rotor 428 within a stator aperture. The first gear 430 may be connected to the rotor 428, and the second gear 432 may engage the first gear 430. The piston 222 may be connected to the second gear 432 by an eccentric gear shaft (not shown) extending from the second gear 432. The longitudinal axis of the eccentric gear shaft may be offset from the axis about which the second gear 432 rotates. The piston 222 may be received within the piston housing 288 connected to the pump body 208. The pump body 208 may be connected to the pump chassis 420 with fasteners that are passed through the various U-shaped halfslots extending from the pump body 208 and received in pump chassis threaded holes 438 (see FIG. 18) defined in the pump chassis 420. The pump inlet body 206 may be connected to the pump body 208 using fasteners 210.

The bracket 434 may be used to connect the stator assembly 426 to the pump chassis 420. In particular, fasteners 442 may be received within holes in the bracket 434. These bracket holes are typically co-axially aligned with stator holes in the stator assembly 426, as well as with pump chassis post apertures formed in two of the pump chassis posts 436 supporting the stator assembly 426, as shown in FIG. 18. As the fasteners 442 are received with the pump chassis post apertures in the posts 436, the stator assembly 426 may be clamped between the pump chassis posts 436 and the bracket 434.

A first alignment shaft 444 (see FIG. 15) may run from the pump chassis 420 to the bracket 434 through the rotor 428 and first gear 430. The rotor 428 and first gear 430 rotate around the longitudinal axis of the first alignment shaft 444. A second alignment shaft 446 (see FIG. 15) may extend through an alignment hole 450 in the pump chassis 420 and through the second gear 432. The second gear 432 rotates around the longitudinal axis of the second alignment shaft 446.

Figure 15:
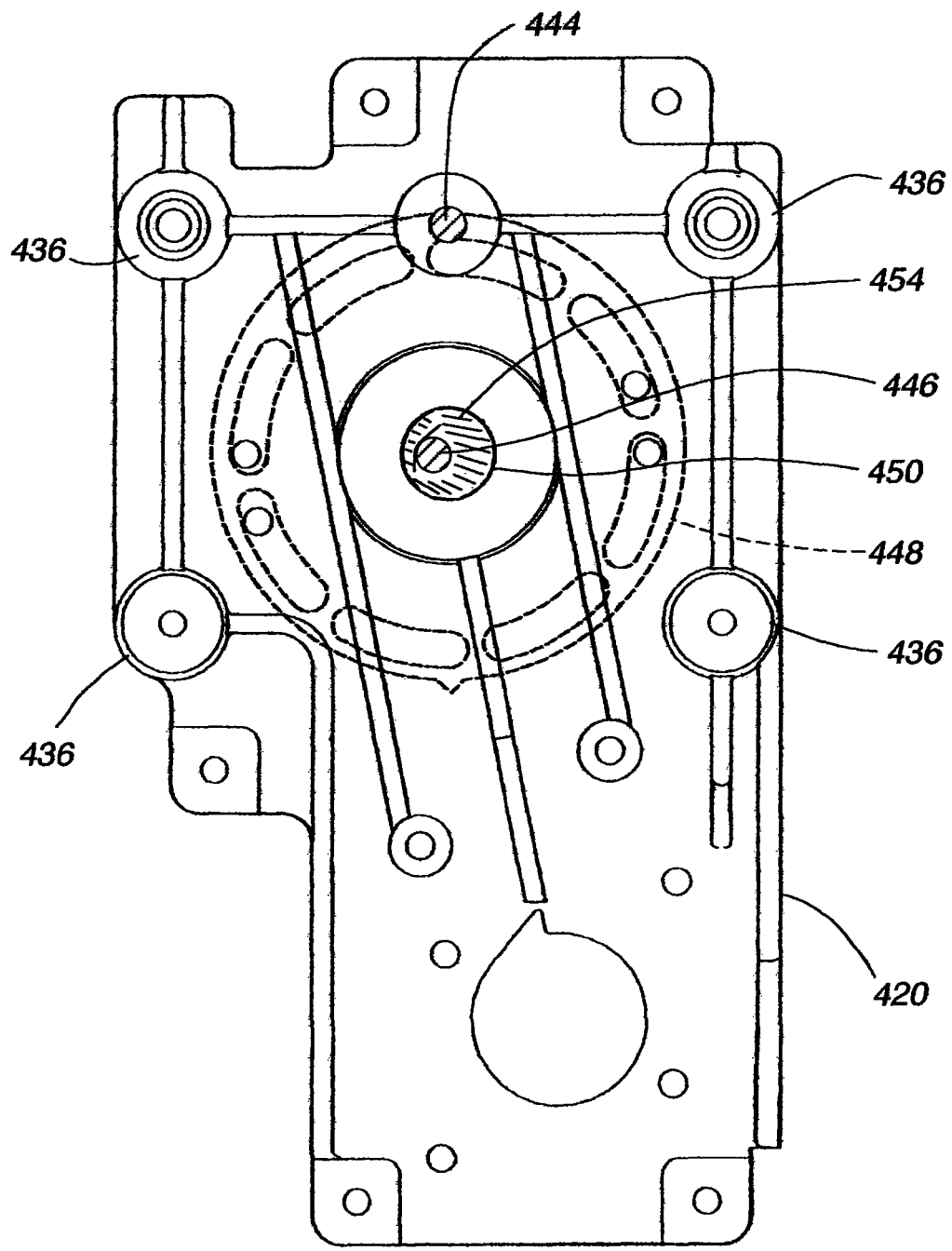
FIG. 15 depicts a top view of the pump chassis showing the first and second alignment shafts.
Figure 17:
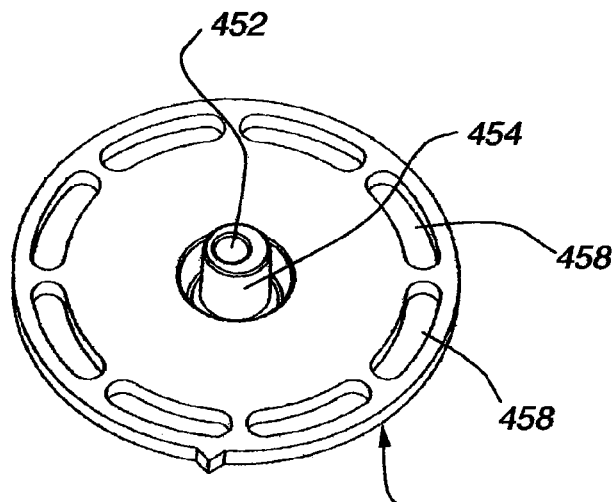
FIG. 17 depicts a perspective view of the eccentric end plate shown in FIG. 16.
Figure 16:
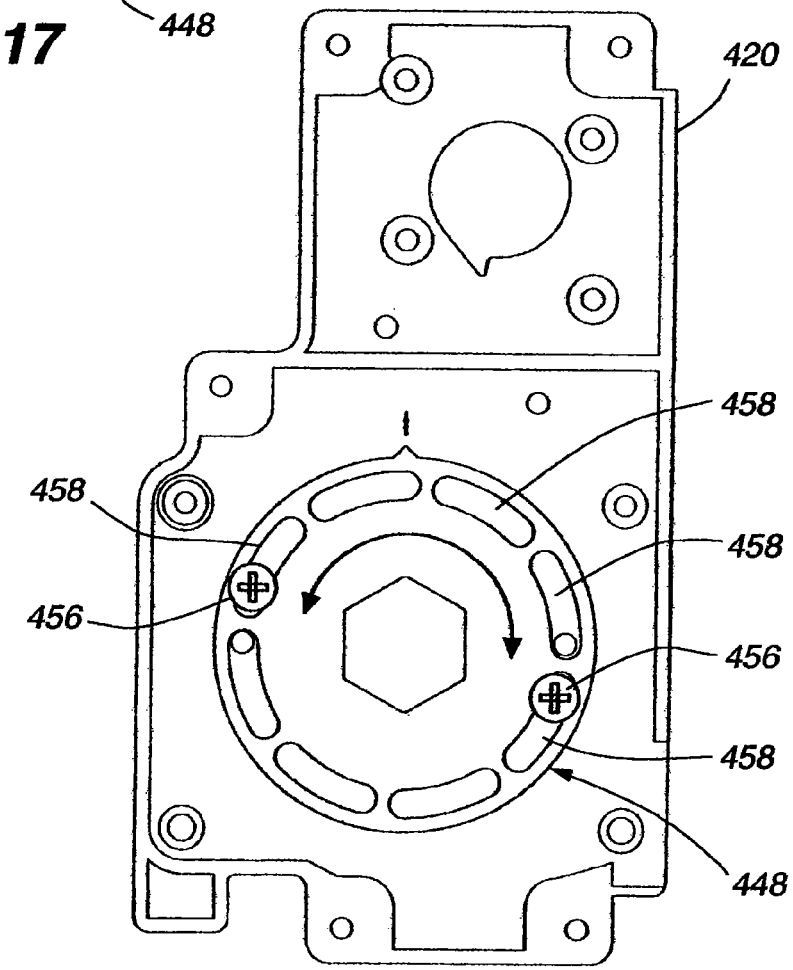
FIG. 16 depicts a bottom view of the pump chassis showing an eccentric end plate connected to the pump chassis.

FIG. 15 depicts a top view of the pump chassis 420 showing first and second alignment shafts 444, 446. FIG. 16 depicts a bottom view of the pump chassis 420 showing an end plate 448 connected to the pump chassis 420. With reference to FIG. 15, the longitudinal axis of the second alignment shaft 446 may be offset with respect to the center of the alignment hole 450 in the pump chassis 420. This may allow the second gear 432 to be adjusted relative to the first gear 430, as described in more detail below. In particular, a bottom end of the second alignment shaft 446 may be received within a shaft receiving hole 452 formed in an extension 454 of the end plate 448 that protrudes through the alignment hole 450. With reference to FIG. 17, the center of the shaft receiving hole 452 may be offset from the center of the end plate extension 454. Generally, this offset causes the center of the shaft receiving hole 452 to be likewise offset from the center of the alignment hole 450 when the end plate extension 454 is received within the alignment hole 450. Thus, the longitudinal axis of the second alignment shaft 446, which coincides with the center of the shaft receiving hole 452, is offset from the center of the alignment hole 450.

Turning to FIG. 16, the end plate 448 may be connected to the pump chassis 420 by fasteners 456 received within pump chassis end plate holes through end plate slotted holes 458. The end plate slotted holes 458 may be spaced around the perimeter of the circular end plate 448. Thus, the end plate 448 may be rotated to multiple positions around the alignment hole 450 while permitting the end plate 448 to be connected to the pump chassis 420. By rotating the end plate 448 around the alignment hole 450, the location of the longitudinal axis of the second alignment shaft 446 may be varied relative to the center of the alignment hole 450.

With reference to FIGS. 15 and 16, the operation of adjusting the gear mesh between the first and second gears 430, 432 will now be described. The end plate 448 may be turned, which also rotates the second alignment shaft 446 within the second alignment hole 450. This changes the location of the longitudinal axis of the second alignment shaft 446 within the alignment hole 450 and the location of the second gear 432 relative to the first gear 430.

In particular, the first alignment shaft 444 remains in a fixed position relative to the center of the alignment hole 450. Thus, the first gear 430 remains in a fixed position relative to the center of the alignment hole 450. Accordingly, changing the relative position of the longitudinal axis of the second alignment shaft 446 relative to the center of the alignment hole 450 changes the relative position of the second alignment shaft 446 relative to the first gear 430. Since the second alignment shaft 446 passes through the center axis of the second gear 432, changing the position of the second alignment shaft 446 relative to the first alignment shaft 444 also adjusts the relative position of the second gear 432 and the first gear 430, thereby permitting the gear mesh between the first and second gears 430, 432 to be adjusted.

Adjusting the gear mesh may help reduce pump noise and wear on the first and second gears 430, 432, insofar as the gear mesh may be finely controlled in order to avoid being too tight or too loose. A sound meter may be used to determine when the second gear 432 has been adjusted to change the mesh between the first gear 430 and second gear 432. Alternatively, a better gear mesh position may be obtained by rotating the end plate 448 until the first and second gears 430, 432 stick together, then slightly backing off this position until the first and second gears 430, 432 can move independently of each other in a vertical direction.

Operation of the pump 200 depicted in FIG. 14 involves moving the switch 38 from the off position to the on position. When the switch 38 is moved, the arm connected to the pump switch connector 384 causes the pump switch connector 384 to move from a first position to a second position within the switch housing 440, thereby closing an electrical circuit with the bobbin assembly 424. Closing the electrical circuit permits electrical power from a power source to be supplied to the bobbin assembly 424 via the power cord 36 connected to the bobbin assembly 424. As power is supplied to the bobbin assembly 424, an electromagnetic field causes the rotor 428 to rotate, thus rotating the first alignment shaft 444 connected thereto and thereby also rotating the first gear 430, which is mounted on the first alignment shaft 444. As the first gear 430 rotates, it causes the second gear 432 to rotate around the second alignment shaft 446. The rotation of the second gear 446 causes the piston 222 mounted to the eccentric gear shaft on the second gear 446 to move back and forth within the piston housing 288. The back and forth motion of the piston 222 causes pulsating, pressurized fluid to be supplied from the reservoir 14 to the tip 24 as described in more detail above. The knob 40, which may be connected to the flow control 216, may be used to adjust the fluid pressure supplied to the tip 24 by the pump 200.

Figure 19:
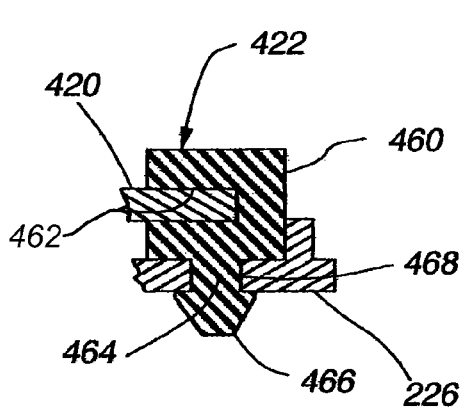
FIG. 19 is a cross-sectional view taken depicting the relationship between the pump chassis, mount, and lower housing segment of the embodiment of Fig., viewed along line 19-19 of FIG. 18.

During operation, the pump 200 may vibrate, thereby generating undesired noise. The pump mounts 422 connecting the pump 200 to the lower base unit segment 226 may be used to reduce pump vibration. As depicted in FIG. 18, the pump 200 may be connected to the lower base unit segment 226 using five pump mounts 422 positioned at corners of the pump chassis 420. Although five pump mounts 422 are shown, more or less may be used. The pump mounts 422 may be composed of rubber or other suitable vibration dampening material. FIG. 19 is a cross-sectional view showing the connections between the pump chassis 420, a pump mount 422, and lower base unit segment 226. As shown in FIG. 19, the pump mount 422 may include a mount body 460 defining a mount aperture 462 for receiving a corner of the pump chassis 420. The pump mount 422 may further include a mount shaft 464 extending from the mount body 460. At the free end of the mount shaft 464, a mount head 466 may be formed, which may generally resemble the profile of a trapezoid with the longer base of the trapezoidal adjacent to the end of the mount shaft 464. The mount shaft and head 464, 466 may be received through a mount connection hole 468 defined in lower base unit segment 226. The trapezoidal profile of the mount head 466 in which shorter side is first received within the mount connection hole 468 enables the mount head 466 to be pushed through the mount connection hole 468 while also generally preventing the mount head 466 from passing back through the mount connection hole 468, thereby maintaining the connection between the pump mount 422 and the lower base unit segment 226. When the pump mounts 422 are received within the lower mount connection holes 468 and the pump chassis corners are received with the mount apertures 462 of the pump mounts 422, the pump chassis 420 may generally be supported a select distance above the lower base unit segment 226. As shown in FIG. 18, the mount body 460 may be generally cubic shaped with one corner rounded. The mount shaft 464 may be generally cylindrical shaped, and the mount head 466 may generally resemble a partial conical shape.

Figure 20:
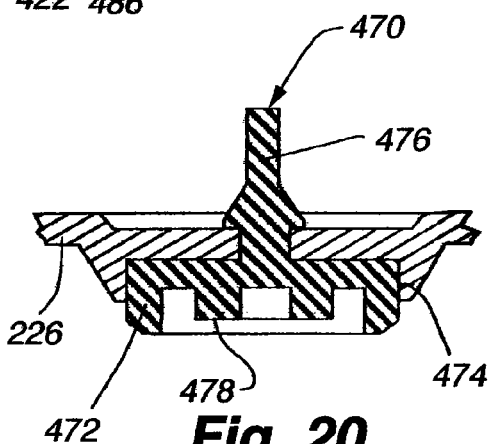
FIG. 20 is a cross-sectional view taken showing the connection between a footing and the lower base unit segment of the embodiment of Fig., viewed along line 20-20 of FIG. 18.

Footings 470 may be used to elevate the outer surface of the lower base unit segment 226 above a surface upon which the lower base unit segment 226 may be supported. Further vibration reduction for the pump 200 may be obtained by use of footings 470 composed of rubber or other suitable vibration dampening material. FIG. 20 is a cross-sectional view, viewed along line 20-20 in FIG. 18, showing the connection between a footing 470 and the lower base unit segment 226. The footing 470 may include a footing body 472 received within a footing aperture 474 defined by lower base unit segment 226. Similar to the pump mount 422, a footing shaft 476 ending in a trapezoidal profile shaped end may extend from the footing body 472. The footing 470 may be connected to the lower base unit segment 226 in a manner similar to that described for the pump mount 422. As shown in FIG. 20, the footing 470 may extend outwardly beyond the footing aperture 474 defined in the lower base unit segment 226, thereby providing a distance between the bearing surface of the footing 470 and the outer surface of the lower base unit segment 226. This distance may result in the lower base unit segment 226 being elevated above the surface upon the footing 470 contacts. The footing body 472 may be generally cylindrical and may include a recessed surface from which a generally circular footing wall 478 may extend.

With reference to FIG. 18, one or more lower base unit columns 480 may extend from the lower base unit segment 226. Each lower base unit column 480 may include a lower base unit column hole 482 for receiving a fastener that may be used to join the upper and lower base unit segments 224, 226 together. Each lower base unit column 480 may be configured to generally co-axially align with a upper base unit column in the upper base unit segment 224 when the upper and lower base unit segments 224, 226 are joined. A U-shaped power cord structure 484 for aligning the power cord 36 with a power cord opening in the upper base unit segment 224 may extend from the lower base unit segment 226. One or more pump alignment walls 486 for aligning the pump chassis 420 within the base unit 12 may also extend from the lower base unit segment 224, and a generally arch-like shell structure 488 defining a partially enclosed tube retainer space 490 for receiving the coiled portion of the tube 34 may extend from the lower base unit segment 226.

Operation of the embodiment depicted in FIGS. 1-20 involves filling the reservoir 14 with a fluid (such as water) and supporting the filled reservoir 14 on the base unit 12. Once the filled reservoir 14 is supported by the base unit 12, fluid may flow through the opened reservoir valve 202 in the reservoir 14 to the pump body 208 as described above.

The pump 200 may be activated using the switch. Once activated, the piston 222 will supply pressurized to the tip 24 as described above.

If the button 30 is engaged during operation of the pump 200, fluid will be prevented from flowing from the tube 34 to the tip 24 as described above, thereby causing the build-up of fluid pressure within the system. This fluid pressure may be relieved by permitting fluid, that otherwise would flow to the tip 24, to flow back to the reservoir 14. As described in more detail above, the fluid pressure will unseat the ball located within the check valve assembly 266, thereby permitting fluid to flow back into the reservoir 14 through the fluid passages in the check valve assembly 266, the pump inlet body 206 and the tube stand 204. When the button 30 is released, the ball 272 reseats within the check valve assembly 266, and the system resumes operation as described above.

All directional references (e.g., upper, lower, upward, downward, left, right, leftward, rightward, top, bottom, above, below, vertical, horizontal, clockwise, and counterclockwise) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected, joined, and the like) are to be construed broadly and may include intermediate members between a connection of elements and relative movement between elements. As such, joinder references do not necessarily infer that two elements are directly connected and in fixed relation to each other.

In some instances, components are described with reference to "ends" having a particular characteristic and/or being connected with another part. However, those skilled in the art will recognize that the present invention is not limited to components which terminate immediately beyond their points of connection with other parts. Thus, the term "end" should be interpreted broadly, in a manner that includes areas adjacent, rearward, forward of, or otherwise near the terminus of a particular element, link, component, part, member or the like. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A dental water jet device pump comprising:
   a pump chassis;
   an end plate adjustably connected to the pump chassis;
   a first alignment shaft;
   a first gear configured to rotate around a longitudinal axis of the first alignment shaft;
   a second alignment shaft rotatably mounted to the end plate; and
   a second gear engaging the first gear and configured to rotate around a longitudinal axis of the second alignment shaft; wherein
   selectively adjusting the end plate relative to the pump chassis selectively adjusts the location of the longitudinal axis of the second alignment shaft relative to the longitudinal axis of the first alignment shaft from a first position to a second position.

2. The dental water jet device pump of claim 1, wherein the end plate is rotatably adjustable relative to the pump chassis.

3. The dental water jet device pump of claim 1, wherein the end plate defines an alignment aperture; and
   the second alignment shaft is disposed within the alignment aperture.

4. The dental water jet device pump of claim 3, wherein the second alignment shaft is positioned eccentrically with respect to a center of the alignment aperture.

5. The dental water jet device pump of claim 1, wherein the first alignment shaft remains substantially fixed when the second gear is moved relative to the first gear.

6. The dental water jet device pump of claim 1, wherein the end plate is secured to the pump chassis via at least one fastener.

7. The dental water jet device pump of claim 1 further comprising a rotor operatively connected to the first gear via the first alignment shaft, wherein the first gear rotates when the rotor rotates.

8. The dental water jet device pump of claim 7 further comprising
   a bobbin assembly operatively connected to the rotor; and
   a power cord electrically connected to the bobbin assembly, wherein the power cord supplies power to the bobbin assembly and when power is supplied to the bobbin assembly the rotor rotates.

9. The dental water jet device pump of claim 8, wherein when the first gear rotates the second gear rotates.

10. The dental water jet device pump of claim 9, further comprising a piston operatively connected to the second gear, wherein when the second gear rotates the piston translates between a first position and a second position.

11. A pump for an oral irrigator comprising:
    a pump chassis;
    a stator supported by the pump chassis;
    a rotor magnetically connected to the stator, wherein when power is supplied to the stator, the stator causes the rotor to rotate;
    a first alignment shaft connected to the rotor;
    a first gear operatively connected to the first alignment shaft, wherein when the rotor rotates the first gear rotates;
    a second gear operatively connected to the first gear, wherein when the first gear rotates, the second gear rotates;
    a second alignment shaft operatively connected to the second gear;
    an alignment plate operatively connected to the pump chassis and operatively connected to the second alignment shaft; wherein selectively moving the alignment plate adjusts the location of a longitudinal axis of the second alignment shaft relative to a longitudinal axis of the first alignment shaft from a first position to a second position.

12. The pump of claim 11, wherein selectively moving the alignment plate relative to the pump chassis selectively moves the second gear relative to the first gear.

13. The pump of claim 11, wherein the second alignment shaft is disposed within an alignment aperture on the alignment plate.

14. The pump of claim 13, wherein the second alignment shaft is positioned eccentrically with respect to a center of the alignment aperture.

15. The pump of claim 14, wherein when the alignment plate is rotated relative to a centerline of the second alignment shaft, the second gear moves relative to the first gear.

16. The pump of claim 11, wherein the alignment plate is rotatably adjustable relative to the pump chassis.

17. The pump of claim 11 further comprising a piston operatively connected to the second gear, wherein when the second gear rotates, the piston translates between a first position and a second position.

18. The pump of claim 11, wherein the alignment end plate is secured to the pump chassis by removable fasteners.

\* \* \* \* \*